United States Patent
Campbell

(10) Patent No.: US 7,423,065 B2
(45) Date of Patent: Sep. 9, 2008

(54) THERAPEUTIC USE OF METHIONINE-DERIVITIVES TO REDUCE THE TOXICITY OF NOISE

(75) Inventor: Kathleen C. M. Campbell, Glenarm, IL (US)

(73) Assignee: Board of Trustees of Southern Illinois University, Springfield, IL (US)

( * ) Notice: Subject to any disclaimer, the term of this patent is extended or adjusted under 35 U.S.C. 154(b) by 438 days.

(21) Appl. No.: 11/324,744

(22) Filed: Jan. 3, 2006

(65) Prior Publication Data

US 2006/0167101 A1 Jul. 27, 2006

Related U.S. Application Data

(60) Division of application No. 09/911,195, filed on Jul. 23, 2001, now Pat. No. 7,071,230, which is a continuation-in-part of application No. 09/057,065, filed on Apr. 8, 1998, now Pat. No. 6,265,386, which is a continuation-in-part of application No. 08/942,845, filed on Oct. 2, 1997, now Pat. No. 6,187,817.

(51) Int. Cl.
*A61K 31/195* (2006.01)
*A61K 31/045* (2006.01)

(52) U.S. Cl. ............................ 514/562; 514/579

(58) Field of Classification Search .................. 514/562
See application file for complete search history.

(56) References Cited

U.S. PATENT DOCUMENTS

| | | | |
|---|---|---|---|
| 2,732,400 | A | 1/1956 | Weiss |
| 3,941,818 | A | 3/1976 | Abdel-Monem |
| 3,962,429 | A | 6/1976 | Furuno et al. |
| 4,426,372 | A | 1/1984 | Borch |
| 4,961,926 | A | 10/1990 | Gabrilove |
| 5,002,755 | A | 3/1991 | Mitchell et al. |
| 5,053,429 | A | 10/1991 | Hirsch et al. |
| 5,122,369 | A | 6/1992 | Dye |
| 5,137,712 | A | 8/1992 | Kask et al. |
| 5,292,773 | A | 3/1994 | Hirsch et al. |
| 5,430,064 | A | 7/1995 | Hirsch et al. |
| 5,466,678 | A | 11/1995 | Kawabata et al. |
| 5,667,791 | A | 9/1997 | Hersh et al. |
| 5,952,367 | A | 9/1999 | Pak |
| 6,177,434 | B1 | 1/2001 | Kopke et al. |
| 6,187,817 | B1 | 2/2001 | Campbell |
| 6,265,386 | B1 | 7/2001 | Campbell |
| 6,649,621 | B2 | 11/2003 | Kopke et al. |
| 7,071,230 | B2 | 7/2006 | Campbell |
| 2004/0110719 | A1 | 6/2004 | Campbell |
| 2004/0127568 | A1 | 7/2004 | Campbell |
| 2005/0090551 | A1 | 4/2005 | Campbell |
| 2007/0105782 | A1 | 5/2007 | Campbell |

FOREIGN PATENT DOCUMENTS

| | | |
|---|---|---|
| EP | 0 008 171 A1 | 2/1980 |
| EP | 0 387 757 A2 | 9/1990 |
| EP | 0 482 493 A2 | 4/1992 |
| EP | 0 620 004 A1 | 10/1994 |
| WO | WO 98/14182 A1 | 4/1998 |
| WO | WO 03/045334 A2 | 6/2003 |

OTHER PUBLICATIONS

Chu et al., Adenosine Triphosphate (ATP) Induces Other Hair Cell Death Abstr. #294, Association for Research in Otolaryngology, Abstracts of the 20th Annual Midwinger Research Meeting, St. Petersburg Beach, Florida, Feb. 2-6, 1997, p. 74.

Whitworth et al., "Alpha-lipoic acid as a protective agent against ototoxicity;" Abstr. No. 532, Abstracts of the 21st Annual Mid-Winter Research Meeting of the Association for Research in Otolaryngology, Feb. 15-19, 1998, p. 134.

Hayes et al., "Amelioration of renal toxicity of high dose cis-platinum diammine dichloride (CPDD) by mannitol induced diuresis," Abstr. No. 676, Proc. Am. Assoc. Cancer Res., p. 169 (1976).

Merrin, "A New method to prevent toxicity with high doses of cis diammine platinum (Therapeutic Efficacy in previously treated widespread and recurrent testicular tumors)," Abstr. C-26, Proc. Am. Assoc. Cancer Res., p. 243 (1976).

Sha et al., "Antioxidant therapy attenuates gentamicin-induced ototoxicity," Abstr. No. 535, Abstracts of the 21st Annual Mid-WInter Research Meeting of the Association for Research in Otolaryngology, Feb. 15-19, 1998, p. 134.

(Continued)

*Primary Examiner*—Cecilia Tsang
*Assistant Examiner*—Kortney Klinkel
(74) *Attorney, Agent, or Firm*—Senniger Powers LLP

(57) ABSTRACT

Methods of preventing or reducing hearing or balance loss and damage to ear cells in patients who have been exposed to toxic levels of noise are provided. These methods comprise administering an effective amount of a methionine protective agent, such as D-methionine, prior to, simultaneously with, or subsequently to exposure to noise. Combinations of these time periods can also be employed.

15 Claims, 6 Drawing Sheets

OTHER PUBLICATIONS

Gessler et al., "Antiradiation effect of S-methylmethionine (Vitamin U)," Prikl. Biokhim. Mikrobiol., 32(6):666-668 (1996).

Campbell et al., "A review of cisplatin protective agents emphasizing nephro- and otoprotectants," Proposed Review Article Not Yet Submitted for Publication, Including Additional Reference Lists.

Dedon et al., "Characterization of the reactions of platinum antitumor agents with biologic and nonbiologic sulfur-containing nucleophiles," Biochemical Pharmacology, 36(12):1955-1964 (1987).

Infante et al., "Chemical radioprotection on biological important compounds," Radiation Research, 67(3):637 (1976).

Gandara et al., Cisplatin chemoprotection and rescue: pharmacologic modulation of toxicity, Seminars in Oncology, 18(1)(suppl.3):49-55 (1991).

Hannermann et al., Cisplatin-induced lipid peroxidation and decrease of gluconeogenesis in rat kidney cortex: different effects of antioxidants and radical scavengers, Toxicology, 51:119-132 (1988).

Schweitzer, "Cisplatin-induced ototoxicity: the effect of pigmentation and inhibitory agents," Laryngoscope, 103:1-52 (1993).

Glover et al., "Clinical trials of WR-2721 and cis-platinum," I.J. Radiation Oncology, Biology, Physics, 16(5):1201-1204 (1989).

Kies et al., "Comparative value of L-, DL-, and D-methionine supplementation of an oat-based diet for humans," J. Nutr., 105:809-814 (1975).

Jones et al., Coadministration of dimethyl sulfoxide reduces cisplatin nephrotoxicity, Anticancer Research, 11:1939-1942 (1991).

Jones et al., Control of nephrotoxicity in the rat during repeated cis-platinum treatments, Journal of Applied Toxicology, 9(4):229-233 (1989).

Jones et al., Control of nephrotoxicity of cisplatin by clinically used sulfur-containing compounds, Fundamental and Applied Toxicology, 18:181-188 (1992).

Speer et al., "Coordination Complexes of Platinum as Antitumor Agents," Cancer Chemotherapy Reports, 59(3)(Pt. 1):629-641 (1975).

Ravi et al., Diethyldithiocarbamate protects against cisplatin ototoxicity and nephrotoxicity, Otolaryngology Head and Neck Surgery, Poster 5, 107(2):232 (1992).

Basinger et al., Dithiocarbamate-induced biliary platinum excretion and the control of cis-platinum nephrotoxicity, Toxicology and Applied Pharmacology, 97:279-288 (1989).

Campbell et al., "D-methionine provides excellent protection from cisplatin ototoxicity in rat," Hearing Research, 102:90-98 (1996).

Campbell et al., D-methionine provides protection against cisplatin damage the rat stria vascularis: a semi-quantitative analysis, Abstr. No. 537, Abstracts of the 21st Annual Mid-winter Research Meeting of the Association for Research in Otolaryngology, Feb. 15-19, 1998, p. 135.

Schein, "Ethyol™ (WR-2721): a chemoprotective agent for platinum anti-cancer drugs," Speaker Abstracts (XP-002053095).

Gandara et al., Evaluation of cisplatin dose intensity: current status and future prospects, Anticancer Research, 9:1121-1128 (1989).

Alden et al., "Exacerbation of cisplatin-induced nephrotoxicity by methionine" Chem.-Biol. Interactions, 48:121-124 (1984).

Ammash et al., "Inactivation of Aminoglycosides Against *Pseudomonas aeruginosa* by a Nutrition Supplementation Solution," Gen. Pharmac., 25(3):461-466 (1994).

Drobnik et al., "Inactivation of bacteriophages with cis-platinum(II) diamminedichloride," Chem.-Biol. Interactions, 11:365-375 (1975).

Newman et al., "Inhibition of Biological Activity of Cisplatin by Thiourea and L-Methionine," J. Clinical Hematology and Oncology, 9(2):208-209 (1979).

Jones et al., Inhibition of cis-diamminedichloroplatinum (II)-induced renal toxicity in the rat Cancer Chemotherapy and Pharmacology, 17:38-42 (1986).

Cardini et al., La radioprotezione dei cromosomi delle midollari umane in vitro, Rabiobiologia Radioterapia E Fisica Medica, 22(6):371-375 (1967).

Basinger et al., "L-methionine antagonism of cis-platinum nephrotoxicity," Toxicology and Applied Pharmacology, 108:1-15 (1990).

Basinger et al., "L-methionine suppresses pathological sequelae of cis-platinum in the rat," Fundamental and Applied Toxicology, 14:568-577 (1990).

Walker Jr et al., "Methods of reduction of cisplatin nephrotoxicity," Annuals of Clinical and Laboratory Science, 11(5):397-409 (1981).

Carrithers et al., "Methylation of Radiation Protector Compounds by Thiol Methyltransferase," FASEB, 5(4):A824 (1991).

Boogaard et al., "4-methylthiobenzoic acid reduces cisplatin nephrotoxicity in rats without compromising anit-tumor activity," Biochemical Pharmacology, 41(12):1997-2003 (1991).

Ward et al., "Modification of the renal toxicity of cis-dichlorodiammineplatinum(II) with furosemide in male F344 rats," Cancer Treatment Reports, 61(3):375-379 (1977).

Zezulka et al., "Nitrogen retention in men fed isolated soybean protein supplemented with L-methionine, D-menthionine, N-acetyl-L-methionine, or inorganic sulfate," J. Nutr., 106:1286-1291 (1976).

Tognella, Pharmacological interventions to reduce platinum-induced toxicity, Cancer Treatment Reviews, 17:139-142 (1990).

Reser et al., "Physiological evidence for protection from cis-platin ototoxicity by D- and L- methionine in vivo," Abstr. No. 203, Abstracts of the 21st Annual Mid-Winter Research Meeting of the Association for Research in Otolaryngology, p. 51, Feb. 15-19, 1998.

Gabaizadeh et al., "Protection of both auditory hair cells and auditory neurons from cisplatin induced damage," Acta Otolaryngol (Stolkholm), 117:232-238 (1997).

Nakano et al., "Protentiation of cisplatin-induced lipid peroxidation in kidney cortical slices by glutathione depletion," Japan J. Pharmacol., 50:87-92 (1989).

Srinivasan et al., "Radioprotection by misoprostol ($PGE_1$ Methyl Analog) In combination with vitamin E, selenomethionine and WR-3689794," Eicosanoids and Other Bioactive Lipids in Cancer, Inflammation and Radiation Injury 2, (K.V. Honn et al. Editors), Plenum Press, NY, pp. 791-797 (1997).

Mekhtiev et al., "Radioprotective effect during the separate and combined use of DL-methionine and thyroxine," Database Chemabs Chemical Abstracts Service, Abstr. No. 76:54431, (1970) (see also Tr. Inst. Fiziol., Akad. Nauk Azerb. SSR, 11:83-100 (1970)).

Correa et al., "Radiosensitization and radioprotection on murine chondrosarcoma" Radiation Research, 74(3):517 (1978).

Jereczek-Fossa et al., "Radiotherapy-induced ear toxicity" Cancer Treatment Reviews, 29:417-430 (2003).

Jones et al., "Relative effectiveness of some compounds for the control of cisplatin-induced nephrotoxicity," Toxicology, 68:227-247 (1991).

Ormond et al., Reduced nephrotoxicity in vivo and in vitro of cisplatin-methionine complex, Brit. J.. Pharmacol. (suppl)., 95:584P (1988).

Melvik et al., "Reduction of cis-dichlorodiammineplatinum-induced cell inactivation by methionine," Inorganica Chemica Acta, 137:115-118 (1987).

Hu et al., "R-phenylisopropyladenosine attenuates noise-induced hearing loss in the chinchilla" Hearing Research, 113:198-206 (1997).

Ravi et al., Relationship of pharmacodynamic effects of cisplatin to the glutathione levels in cochlea, inferior colliculus and kidney, Pharmacologist, Abstract D-19 402, 33(3):217 (1991).

Korver et al., "Round window application of D-methionine provides cisplatin otoprotection," Abstr. No. 356, Abstracts of the 21st Annual Mid-Winter Research Meeting of the Association for Research in Otolaryngology, Feb. 15-19, 1998, p. 135.

Montine et al., "Role of Endogenous sulfur-containing nucleophiles in an in vitro model of cis-Diamminedichloroplatinum(II)-induced nephrotoxicity," Biochemical Pharmacology, 39(11):1751-1757 (1990).

De Vechhi, Sperimentazione clinica di una nuova sostanza radioprotettiva (Cloruro Di Metilmetionin-Sulfonio), Radiobiologia Radioterapia E Fisica Medica, 22(5):355-370 (1967).

Stedman's Medical Dictionary, "Preventive" and "Prophylactic," Williams and Wilkins Co., 22nd Ed., pp. 1017, 1025 (1972).

Salikhodzhaev et al., "Stimulation of postirradiation recovery of rat haemopoiesis by a cobalt preparation," Database Biosis Biosciences Information Service, Philadelphia, PA, Abstr. No. 08095385 (see also Radiobiologya, 31(6):835-837 (1991).

Rho et al., "Structural evidence for protection from cisplatin ototoxicity by both D- and L- methionine in vivo," Abstr. No. 202, Abstracts of the 21st Annual Mid-Winter Research Meeting of the Association for Research in Otolaryngology, Feb. 15-19, 1998, p. 51.

Burchenal et al., Studies of cross-resistance, synergistic combinations and blocking of activity of platinum derivatives, Biochimie, 60(9):961-965 (1978).

Kovacs et al., Study of the radiation protection effect of selenium-methionine by determining the paramagenetic properties of liver tissues of mice, Acta Physica Hungarica, 64(1-3):321-326 (1988).

Romito, "Sulla radioprotezione cromosomica in vitro: esperienze con metionina, acido aspartico, leucina, lisina," Fracastoro, 62(6):576-581 (1969).

Friedman et al., "The blocking of the tetrachloroplatinate(II) inhibition of malate dehydrogenase by sulfur-containing amino acids," Biochimica et Biophysica Acta, 341:277-283 (1974).

Church et al., The comparative effects of sodium thiosulfate, diethyldithiocarbamate, fosfomycin and WR-2721 on ameliorating cisplatin-induced ototoxicity, Hearing Research, 86(1,2):195-203 (1995).

Drewinko et al., "The effect of cis-diamminedichloroplatinum(II) on cultured human lymphoma cells and its therapeutic implications," Cancer Research, 33:3091-3095 (1973).

Kido, "The influence of methylmethionine sulfonium chloride (MMSC) on survivors of mice after X-ray irradiation, especially the consideration of the drug effect for the degeneration of intestinal mucosa," Kansai Ika Daigaku Zasshi, 25(1):104-107 (1973).

Deegan et al., The nephrotoxicity, cytotoxicity and renal handling of a cisplatin-methionine complex in male Wistar rats, Toxicology, 89:1-14 (1994).

Boogaard et al., "The role of methallothionein in the reduction of cisplatin-induced nephrotoxicity by $Bi^{3+}$-pretreatment in the rat in vivo and in vitro, are antioxidant properties of methallothionein more relevant than platinum binding?," Biochemical Pharmacology, 41(3):369-375 (1991).

Molteni et al. "The use of S-adenosyl-methionine as a radioprotective agent," Gazzetta Medica Italiana, 137(7-8):303-308 (1978).

Friedman et al., The Utilization and Safety of Isomeric Sulfur-Containing Amino Acids in Mice, J. Nurt., 114:2301-2310 (1984).

Jones et al., Thioether suppression of cisplatin nephrotoxicity in the rat, Anitcancer Research, 11:449-454 (1991).

Jones et al., "Thiol and thioether suppression of cis-platinum-induced nephrotoxicity in rats bearing the Wlker 256 Carcinosarcoma," Anticancer Research, 9:1937-1942 (1989).

Gentile-Ramos, "Treatment of diaper erythema with methionine" Archivos De Pediatria Del Uruguay, 36(8):519-528 (1965).

Kopke et al., Use of organotypic cultures of Corti's organ to study the protective effects of antioxidant molecules on cisplatin-induced damage of auditory hair cells, The American Journal of Otology, 18:559-571 (1997).

Printen et al., "Utilization of D-methionine during total parenteral nutrition in postsurgical patients," The American Journal of Clinical Nutrition, 32:1200-1205 (1979).

Treskes et al., "WR2721 as a modulator of cisplatin- and carboplatin-induced side effects in comparison with other chemoprotective agents: a molecular approach," Cancer Chemotherapy and Pharmacology, 33:93-106 (1993).

Van De Water et al., Oxidatives stress in the inner ear: combinatorial therapy; Abstr. No. 6, Abstracts of the 21st Annual Mid-Winter Research Meeting of the Association for Research in Otolaryngology, Feb. 15-19, 1998, p. 2.

Budavari, S., et al., The Merck Index, An Encyclopedia of Chemicals, Drugs, and Biologicals, 1989, Merck & Company, Inc., Eleventh Edition, Scientific & Technical Information Center, Jan. 6,1993, Patent and Trademark Office.

Gass, A.E., et al., Effect of Stereoisomers of Sulfur-containing Amino Acids on Local Skin Protection in X-irradiated Mcie, Aerospace Medicine, Jul. 1967, pp. 708-712.

Jacobs, J.B., et al., Treatment of Radiation-induced alopecia, Head Neck Surg., Nov.-Dec. 1979, vol. 2(2), pp. 154, Entrez PubMed.

Remington's Pharmaceutical Sciences "Structure Activity Relationship and Drug Design" Chapter 27, A. Osol et al., Editors, Mack Publishing (1980) pp. 420-435.

Stedman's Medical Dictionary, "Radiation," Williams and Wilkins Company, 22nd Ed., (1972) p. 1058.

THERAPEUTIC USE OF METHIONINE-DERIVITIVES TO REDUCE THE TOXICITY OF NOISE

REFERENCE TO RELATED APPLICATIONS

This patent application is a divisional application of recently allowed U.S. patent application Ser. No. 09/911,195, filed Jul. 23, 2001, which is a continuation-in-part of U.S. patent application Ser. No. 09/057,065, filed Apr. 8, 1998, now U.S. Pat. No. 6,265,386, which is a continuation-in-part of U.S. Ser. No. 08/942,845, now U.S. Pat. No. 6,187,817. The entire contents of which are incorporated herein by reference.

BACKGROUND OF THE INVENTION

1. Field of the Invention

The present invention relates to the use of protective agents in cancer chemotherapy in human and animal subjects. Protective agents are compounds that prevent, reduce, or otherwise ameliorate the toxic side effects of anti-cancer chemotherapeutic compounds in normal body cells while substantially preserving the anti-tumor properties of these compounds in vivo when administered prior to, concomitantly with, or subsequently to administration of such chemotherapeutic compounds. More specifically, the present invention relates to the use of D-methionine and structurally related compounds as protective agents having oto-protective, weight loss-protective, gastrointestinal-protective, neuroprotective, alopecia-protective, and survival-enhancing effects in conjunction with chemotherapy employing platinum-containing anti-neoplastic agents, such as cisplatin. The present invention also relates to the use of D-methionine and structurally related compounds as protective agents having oto-protective effects against noise-induced, loop diuretic-induced, aminoglycoside antibiotic-induced, iron chelator-induced, quinine- and quinidine-induced, and radiation-induced hearing loss, as well as protective effects in ameliorating other radiation-induced side effects such as neural damage, alopecia, gastrointestinal disorders, and reduced patient survival.

2. Description of Related Art

Cisplatin Chemotherapy

Cisplatin (cis-diamminedichloroplatinum(II); CDDP) is a widely used antineoplastic agent. Cisplatin administration has increased both in the variety of cancer types for which it is employed and in the amount used in a given individual to achieve maximal therapeutic effect (Blumenreich et al., 1985; Forastiere et al., 1987; Gandara et al., 1989).

The toxic side effects of cisplatin have long been recognized and are widely reported (Lippman et al., 1973; also see the review by Hacker, 1991). These toxicities include a variety of peripheral neuropathies, myelo-suppression, gastrointestinal toxicity, nephrotoxicity, and ototoxicity (Ozols and Young, 1985; Stewart et al., 1987; Stoter et al., 1989). Initially, the primary dose-limiting factor was nephrotoxicity, but now the routine administration of mannitol, hypertonic saline, and high fluid administration have ameliorated, but not eliminated, that side effect. However, ototoxicity remains uncontrolled (Bajorin et al., 1987; Fillastre and Raguenez-Viotte, 1989). Although nephrotoxicity can still be dose-limiting, currently the primary dose-limiting factor is ototoxicity (Blumenreich et al., 1985; Forastiere et al., 1987; Berry et al., 1990).

The primary ototoxic effects of cisplatin appear to occur in the cochlea. Anatomical changes occur in both the stria vascularis and the organ of Corti. The primary histologic findings include hair cell degeneration and damage to the supporting cells that are dose-related (Anniko and Sobin, 1986). At high doses, total collapse of the membranous labyrinth can occur (Anniko and Sobin, 1986). In the organ of Corti, there is loss of outer and inner hair cells, with a propensity for outer hair cell loss in the basal turn (Fleischman et al., 1975; Komune, 1981; Estrem et al., 1981; Schweitzer, 1993), and alterations in the supporting cells and Reissner's membrane (Komune, 1981; Estrem et al., 1981). Estrem et al. (1981) also reported softening of the cuticular plate and an increased number of lysosomal bodies in the apical portion of the outer hair cell. However, the mechanisms inducing these changes are largely unknown.

For equivalent inner ear concentrations, cisplatin is the most ototoxic drug known (Moroso and Blair, 1983; Koegel, 1985; Anniko and Sobin, 1986; Griffin, 1988). Generally, cisplatin ototoxicity is irreversible, its onset insidious, and the hearing loss may progress after discontinuation of the protocol (Schaefer et al., 1985; Melamed et al., 1985; Pollera et al., 1988; Aguilar-Markulis et al., 1981; see the review by Moroso and Blair, 1983). Hearing loss is usually permanent (Vermorken et al., 1983). Partial recovery may occur in some cases, but only one of 121 patients with hearing loss had complete recovery in a study by Aguilar-Markulis et al., (1981). Hearing loss typically starts at the ultra high frequencies (9000 to 20000 Hz) (Fausti et al., 1984; Kopelman et al., 1988) and then progresses into the high conventional audiometric range (Laurell and Engström, 1989; Kopelman et al., 1988; Meyer, 1989), reducing the patient's ability to hear consonant but not vowel sounds. An inability to understand speech and tinnitus are frequent complaints (Kopelman et al., 1988). An increasing number of patients survive chemotherapy, but frequently with hearing impairment.

Nucleophilic Sulfur Protective Agents

Many sulfur-containing compounds (including substances with thio, thiol, and thioether groups) have been reported to provide CDDP nephroprotection in animal models (Anderson et al., 1990; Jones and Basinger, 1989; Jones et al., 1986; 1991a, b, c; 1992). These compounds may act by preventing the CDDP-induced depletion of glutathione or the binding of CDDP to protein sulfhydryl groups (Hanneman and Baumann, 1988; Nakano and Gemba, 1989; Gandara et al., 1989; Ravi et al., 1991; Schweitzer, 1993).

Additionally, sodium thiosulfate (STS) and diethydithiocarbamate (DDTC) provide good CDDP otoprotection in animals (Otto et al., 1988; Church et al., 1995; Rybak et al., 1995). Unfortunately, STS may reduce CDDP tumoricidal action (Pfeifle et al., 1985; Aamdal et al., 1987) and may exacerbate CDDP-induced weight loss and mortality (Otto et al., 1988). DDTC does not interfere with antitumor action (Qazi et al., 1988; Berry et al., 1989; Dedon et al., 1984; Borch et al., 1988), but can produce severe side effects (Rothenberg et al., 1988; Qazi et al., 1988).

D-Methionine

D-methionine (D-Met) is a sulfur-containing nucleophile that provides highly effective CDDP nephroprotection in animals without decreasing anti-tumor action (Jones and Basinger, 1989). Although only tested in that single study at a single dose level, D-Met was the most effective CDDP nephroprotectant that did not interfere with CDDP tumoricidal action out of nearly 40 sulfur-containing agents tested in a series of studies by Jones and colleagues (Jones and Basinger, 1989; Jones et al., 1986; 1991a, b, c; 1992). As far as the inventor is aware, D-Met has never been previously tested as a CDDP otoprotectant, and has not yet been tested clinically (Treskes and van der Vijgh, 1993).

Sulfur-Containing Protective Agents and the Modulation of Cisplatin-Induced Toxicity Studies indicate that individual sulfur-containing protective agents may only be effective in reducing specific types of toxicity, such as nephrotoxicity, while remaining ineffective in blocking other platinum-related complications such as peripheral neuropathy and ototoxicity (Schweitzer, 1993). In addition, an agent which is effective as a regional chemoprotector following site-specific (intraperitoneal) usage of platinum-containing compounds such as CDDP may fail to provide adequate systemic protection, or may inhibit antitumor activity (Schweitzer, 1993).

Not all sulfur-containing compounds provide protection against all of CDDP's toxicities, and it is not possible to predict which protective agents will be effective or ineffective for this purpose. For example, cefoxitin (Jones et al., 1992) does not provide nephroprotection. Ethyl-L-cysteinate and N-(2-mercapto-propionyl)glycine (Jones and Basinger, 1989) exacerbate CDDP nephrotoxicity. 2-(methylthio)nicotinic acid does not provide nephroprotection in rats (Jones et al., 1991b). The sodium salt of penicillin G does not protect against CDDP nephrotoxicity or weight loss (Jones et al., 1992). Similarly, thiamine-HCl does not protect against cisplatin nephrotoxicity or weight loss (Jones et al., 1992).

Furthermore, sulfur-containing compounds protective against one type of CDDP toxicity frequently do not protect against other CDDP toxicities, and it is not possible to predict the specific antitoxic effectiveness of such compounds. Cephalexin (Jones et al., 1992) protects against CDDP-induced kidney dysfunction and weight loss, but curiously does not prevent kidney pathology. Cefoxitin (Jones et al., 1992) provides some protection against CDDP-induced weight loss, but does not protect against CDDP nephrotoxicity. The sodium salt of penicillin G does not protect against either CDDP-induced nephrotoxicity or weight loss (Jones et al., 1992). Sulfathiazole provides protection against CDDP nephro- toxicity, but not weight loss (Jones et al., 1992).

WR2721 provides excellent CDDP nephroprotection (Mollman et al., 1988), but does not ameliorate nausea and vomiting (Glover et al., 1987). Nor does WR2721 seem to provide CDDP otoprotection: Glover et al. (1987) found mild to severe hearing loss in 20 of 36 patients receiving WR2721 prior to CDDP although nephroprotection was obtained. Rubin et al. (1995) reported a 45% incidence of significant hearing threshold shift in patients pretreated with WR2721 prior to CDDP administration. Unfortunately, neither the Glover et al. (1987) nor Rubin et al. (1995) studies employed a control group, and both reported a high incidence of ototoxicity in patients receiving WR2721. In hamsters, Church et al. (1995) reported no WR2721 protection from ototoxicity or mortality.

Even when a sulfur-containing agent is found to be protective, its side effects can be so severe that clinical applicability is precluded. In addition, even among agents that provide CDDP otoprotection, the protection may be so inconsistent and/or the side effects so great that they would not be used clinically. For example, DDTC provides protection against CDDP-induced nephrotoxicity (Qazi et al., 1988; Berry et al., 1989; Gandara et al., 1989a, 1989b, and 1991) and ototoxicity (Church et al., 1995), but the protection against ototoxicity may only be partial (Gandara et al., 1989a; Ravi et al., 1992) and its side effects are severe (Rothenberg et al., 1988; Berry et al., 1990). If DDTC dosing is reduced to ameliorate its side effects, adequate protection from CDDP side effects may not occur (Paredes et al., 1988). Similarly, disulfiram (Antabuse), which can be used as a precursor for its metabolite DDTC, can cause sensorimotor neuropathy (Argov and Mastiglia, 1979) and reversible confusion that can be dose-limiting (Stewart et al., 1987). Consequently, it is unlikely that DDTC will be widely used clinically as a CDDP chemoprotectant. In contrast, as described below, D-Met provides complete otoprotection without apparent adverse side effects.

Finally, many sulfur-containing compounds inhibit the anti-tumor action of CDDP, and it is not possible to predict which agents will or will not act in this manner. Thus, many agents that provide CDDP protection are not clinically useful. For example, Captropril (Jones et al., 1992) protects against CDDP nephrotoxicity, but reacts immediately with CDDP to form a precipitate if coadministered, thereby precluding antitumor efficacy. L-methioninamide (Jones et al., 1991b) provides excellent CDDP nephroprotection, but impairs CDDP anti-tumor action. Metallothionein, a sulfur-containing compound the synthesis of which is induced by administration of bismuth subnitrate, provides CDDP nephroprotection, but also inhibits CDDP anti-tumor action (Naganuma et al., 1987; Boogaard et al., 1991; Satoh et al., 1993; Imura et al., 1992; Endresen et al., 1994). STS reduces CDDP nephrotoxicity (Pfeifle et al., 1985; Howell et al. 1982) and ototoxicity (Otto et al., 1988; Church et al., 1995), although some authors report inadequate otoprotection (Markman et al., 1985). However, STS will probably not be clinically useful as coadministration with CDDP reduces the latter's tumoricidal action (Pfeile et al., 1985; Aamdal et al., 1987; Jones et al., 1991b), and two route administration does not provide nephroprotection (Jones et al., 1991b). Even in the absence of other agents, STS may also increase mortality and induce weight loss (Otto et al., 1988). Biotin, another sulfur-containing compound that provides good CDDP nephroprotection, inhibits anti-tumor activity (Jones et al., 1992).

Thus, a variety of sulfur-containing compounds can act as protective agents for particular toxicities. A comparison of C—SH— and C—S—C-containing compounds demonstrated that the C—S—C— group was more effective in preventing nephrotoxicity in rats (Jones et al., 1989). However, not all of the compounds possessing the C—S—C— group were found to be effective cisplatin antagonists.

The foregoing discussion demonstrates that it is not possible to predict reliably which particular sulfur-containing nucleophile will exhibit a platinum-containing compound protective effect in any particular type of cell, tissue, or organ. Indeed, individual compounds seem to exert their protective effects only in certain tissues. Thus, the ability of any particular nucleophilic sulfur compound to act as a protective agent in any particular tissue can only be determined by direct experimentation. Of course, such compound will only be of value if it does not substantially reduce the anti-tumor efficacy of cisplatin or related anti-tumor platinum-containing compounds.

Deegan et al. (1994) demonstrated that male Wistar rats receiving a single intraperitoneal dose of cisplatin-methionine at a 1:5 ratio by weight did not exhibit cisplatin-induced nephrotoxicity. Their results indicated that cisplatin-methionine is significantly cytotoxic, yet lacks cisplatin-associated renal toxicity. These workers suggested a role for either methionine co-treatment or cisplatin-methionine compounds in the treatment of human cancers. However, they neither disclosed nor suggested the specific otoprotective, weight loss-protective, gastrointestinal-protective, neuroprotective, alopecia-protective, or survival-enhancing effects of D-methionine surprisingly discovered by the present inventor. Nor did they provide any motivation to investigate D-methionine as an otoprotectant, weight loss-protectant, survival-enhancing agent, etc., or any reasonable expectation that methionine could act in these manners during cisplatin administration. Finally, Deegan et al. provided no guidance or suggestion as to how methionine could be used as a protective agent for various toxicities in humans, as described herein. As noted by Schweitzer (1993; page 12), while various nucleophilic sulfur protective agents have been shown to be effective in blocking or reversing the renal toxicity of CDDP while retaining the chemotherapeutic activity of the drug, each agent has to be considered individually. The effects on antineoplastic activity, individual CDDP toxicities, and appropriate dosing schedules need to be determined on a per se basis for each compound.

In view of the foregoing, the utility of D-Met as a highly effective platinum-containing anti-neoplastic agent otoprotectant, weight loss protectant, gastrointestinal protectant, neuroprotectant, alopecia protectant, and survival-enhancing agent which does not interfere with anti-tumor activity, and which does not appear to cause any serious side effects, could not have been predicted. In fact, the discovery of D-Met's beneficial effects is surprising in view of the many significant problems, discussed above, encountered with previously described sulfur-containing nucleophiles that preclude their clinical use.

SUMMARY OF THE INVENTION

The present inventor has addressed the long-felt need in the art for protective agents effective in preventing or ameliorating various toxic effects of cisplatin and other platinum-containing anti-tumor compounds, but which do not significantly affect the antineoplastic activity of these compounds, and which do not themselves cause deleterious side effects as a result of their administration. She has also addressed the long-felt need in the art for protective agents effective in preventing or ameliorating various toxic effects of aminoglycoside antibiotics, loop diuretics, iron chelating agents, quinine, quinidine, noise, and radiation. She has surprisingly discovered that D-methionine, and structurally related compounds, can be used as an otoprotectant, a weight loss protectant, a gastrointestinal protectant, a neuroprotectant, an alopecia protectant, and a survival-enhancing agent during treatment of a mammal with such compounds, or due to exposure to noise or radiation.

Accordingly, in one aspect, the present invention provides a method for preventing or reducing ototoxicity in a patient undergoing treatment with an aminoglycoside antibiotic, comprising administering to the patient an anti-ototoxic effective amount of a methionine protective agent.

In another aspect, the present invention provides a method for preventing or reducing ototoxicity in a patient undergoing treatment with a loop diuretic agent, comprising administering to the patient an anti-ototoxic effective amount of a methionine protective agent.

In a further aspect, the present invention provides a method for preventing or reducing ototoxicity in a patient undergoing treatment with an iron chelating agent, comprising administering to the patient an anti-ototoxic effective amount of a methionine protective agent.

In yet a further aspect, the present invention provides a method for preventing or reducing ototoxicity in a patient undergoing treatment with quinine or quinidine for conditions in which such compounds are indicated, comprising administering to the patient an anti-ototoxic effective amount of a methionine protective agent.

In another aspect, the present invention provides a method for preventing or reducing ototoxicity in a patient exposed to noise for a time and at an intensity sufficient to result in ototoxicity, comprising administering to the patient an anti-ototoxic effective amount of a methionine protective agent.

In yet another aspect, the present invention provides a method for preventing or reducing ototoxicity, neurotoxicity, alopecia, gastrointestinal disorder, or reduced survival in a patient exposed to radiation for a time and at an intensity sufficient to result in ototoxicity, neurotoxicity, alopecia, gastrointestinal disorder, or reduced survival, comprising administering to the patient an effective amount of a methionine protective agent.

The present invention also provides compositions, including pharmaceutical compositions, comprising the present methionine protective agents, either alone, or in combination with an aminoglycoside antibiotic, a loop diuretic agent, an iron chelating agent, quinine, or quinidine.

Such protective agents can be administered prior to, simultaneously with, or subsequently to administration of the aminoglycoside antibiotic, loop diuretic agent, iron chelating agent, quinine, quinidine, or exposure to a toxic level of noise or radiation. Combinations of these time periods can also be employed.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which.

DETAILED DESCRIPTION OF THE PREFERRED EMBODIMENTS

Figure 1A:
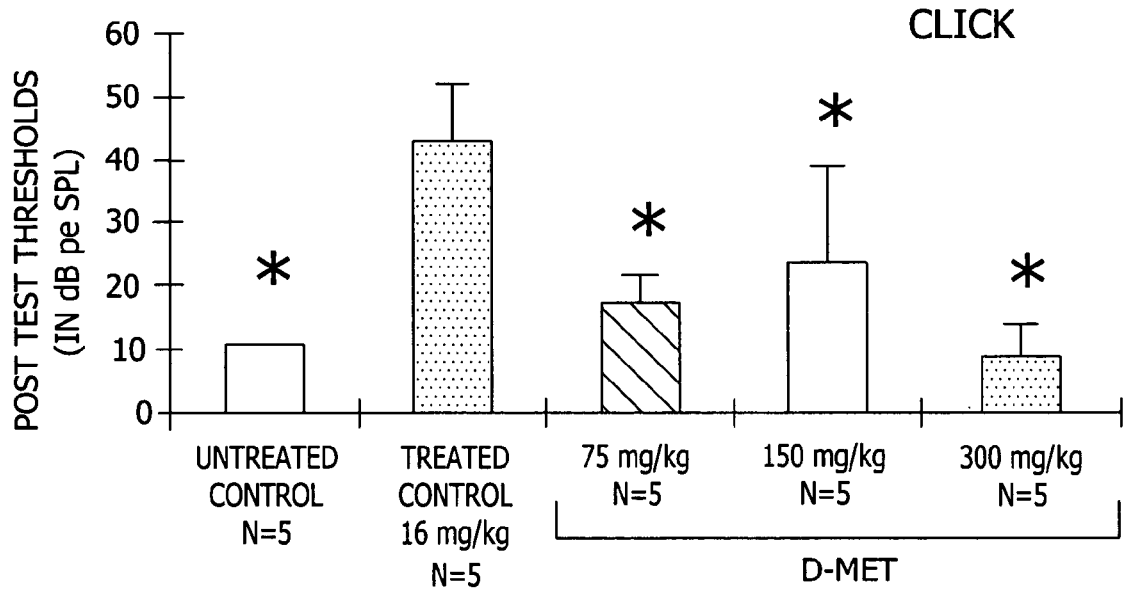
FIG. 1 shows ABR post-test thresholds (means±1 S.D.) for the various animal groups for all stimuli including: a) clicks; b) 1000 Hz tonebursts; c) 4000 Hz tonebursts; d) 8000 Hz tonebursts; and e) 14000 Hz tonebursts. * indicates significantly different from the CDDP-treated controls at the $p \leq 0.01$ level.
Figure 1B:
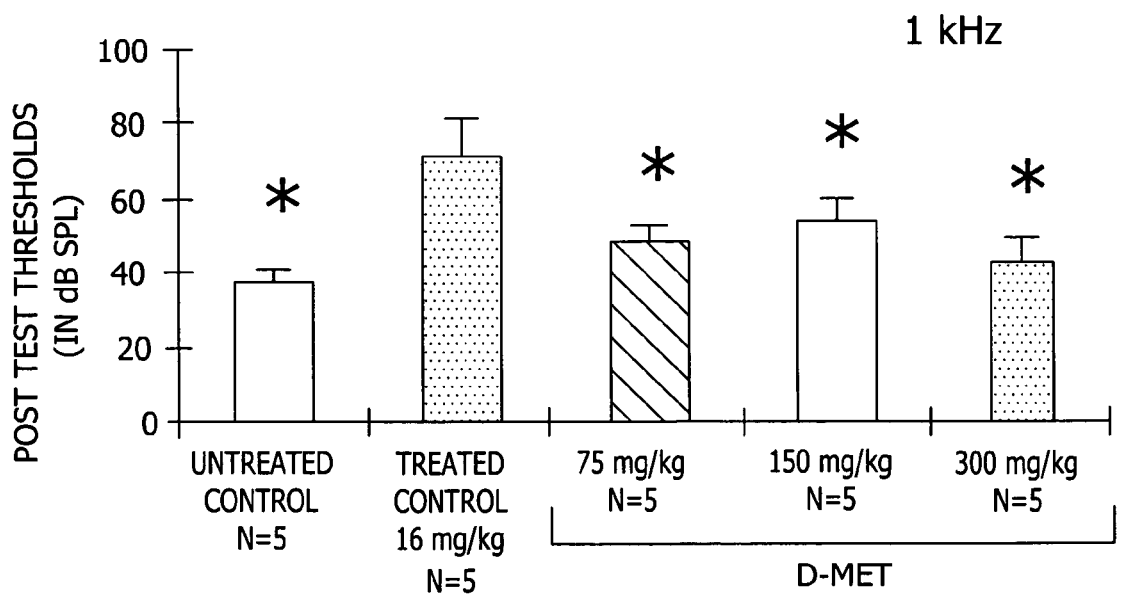
Figure 1C:
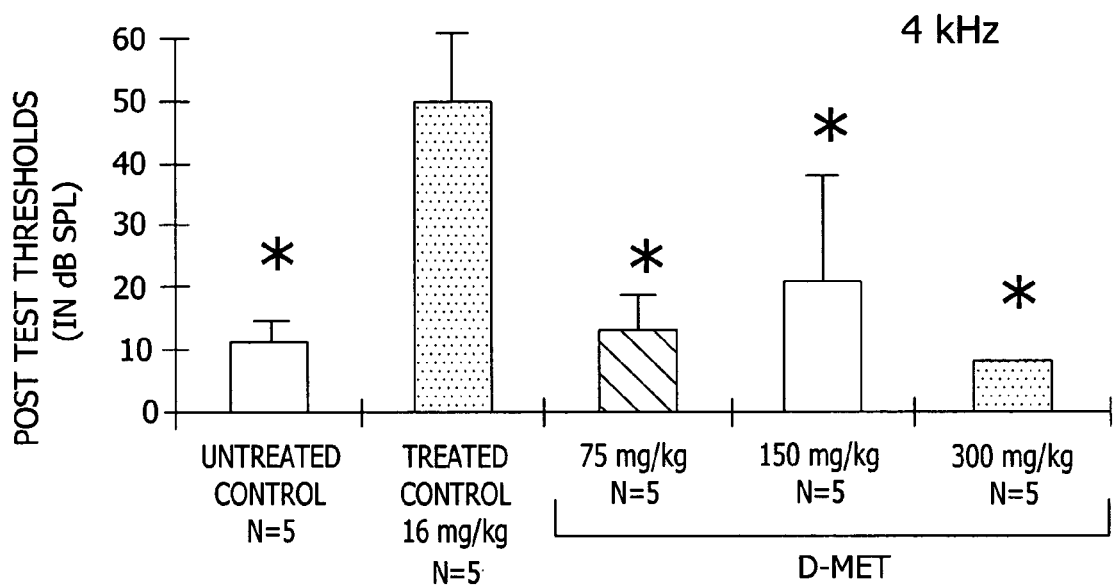
Figure 1D:
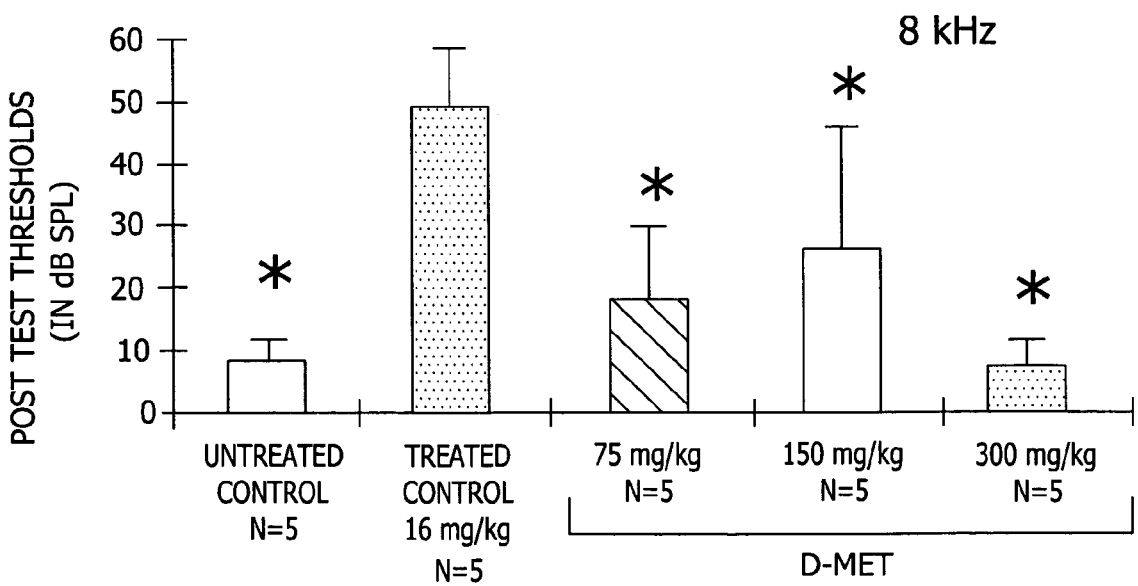
Figure 1E:
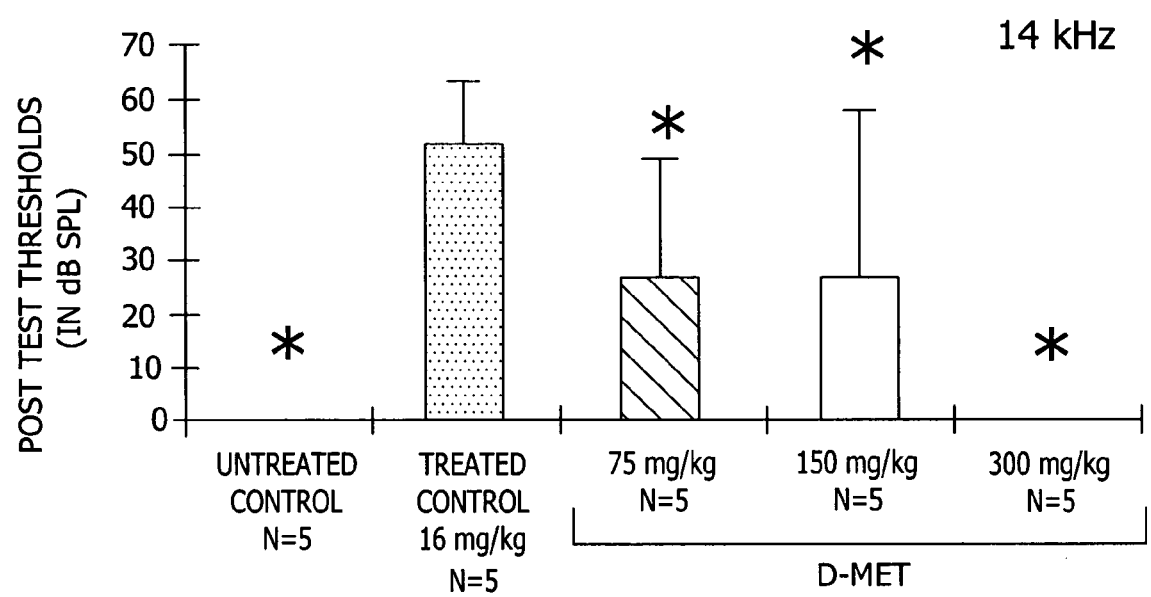
Figure 2A:
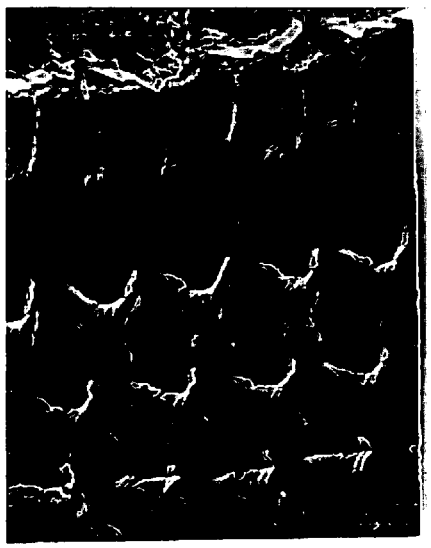
FIGS. 2A-2F are SEM photomicrographs of: A) middle turn of untreated control; B) middle turn of treated control (16 mg/kg CDDP); C) middle turn of animal administered 300 mg/kg D-Met prior to the 16 mg/kg CDDP dose; D) basal turn of untreated control; E) basal turn of treated control (16 mg/kg CDDP); and F) basal turn of animal administered 300 mg/kg D-Met prior to the 16 mg/kg CDDP dose.
Figure 2B:
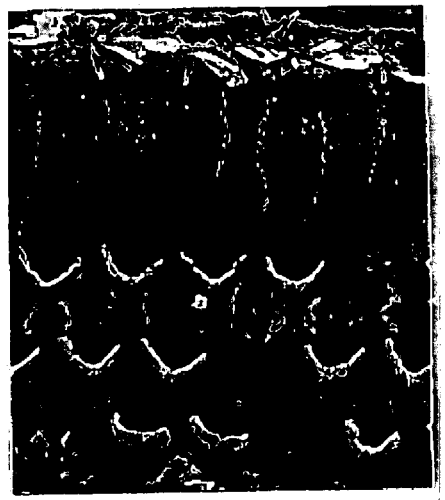
Figure 2C:
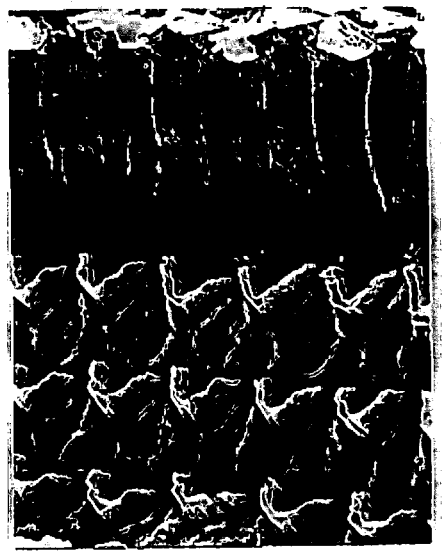
Figure 2D:
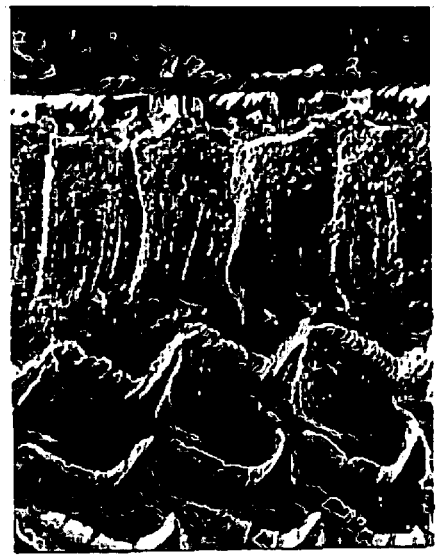
Figure 2E:
Figure 2F:
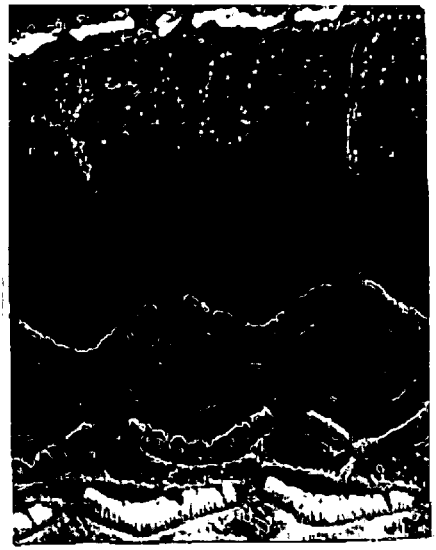

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

EXAMPLE 1

Otoprotective Effect of D-Met

This experiment demonstrates the effectiveness of D-Met in preventing a variety of different toxic side effects associated with the use of platinum-containing anti-tumor compounds, exemplified by CDDP (cisplatin), in a mammal.

Materials and Methods

Animals

As is well known to those of ordinary skill in the art, the rat is a well-accepted experimental animal useful as a model for studies of CDDP toxicity in humans.

Complete data sets were obtained for five groups of five male Wistar rats (280-421 g). All animals were anesthetized with 1 ml/mg IM of Rompun cocktail (a solution containing 86.21 mg/ml ketamine and 2.76 mg/ml xylazine) prior to all injections and testing. Anesthesia was supplemented as needed with half doses throughout testing. The five groups included: a treated control group which received 16 mg/kg CDDP dissolved in normal sterile saline (1 mg of CDDP/ml normal saline; solution pH 6.3) administered by i.p. infusion with a Harvard Apparatus Infusion Pump, over a 30 minute period, an untreated control group that received an equivalent volume of normal saline (pH 6.5) instead of CDDP, and three experimental groups that received either 75, 150, or 300 mg/kg D-Met dissolved in 3-5 ml of normal saline (solution pH 6.6) delivered by slow (over 1-2 minutes) i.p. injection 30 minutes prior to the same CDDP infusion as the treated control group. Both CDDP (purchased from Sigma Chemical Co., St. Louis) and D-Met (purchased from Acros Organics, Pittsburgh, Pa.) were freshly prepared before each experiment. For the treated control group, a total of 10 animals were needed to obtain 5 animals with complete data sets because 50% of the animals did not survive to the end of the study period. Only 5 animals were needed in the untreated control and in each of the D-Met pretreated groups because all of the animals in each of those groups survived until the end of the study period.

All of the care and use of the animals was approved by the Southern Illinois University School of Medicine Laboratory Animal Care and Use Committee, and was under the supervision of the Southern Illinois University School of Medicine Unit for Laboratory Animal Medicine.

Evoked Potentials

Auditory Brainstem Testing (ABR) was used to assess auditory threshold. Testing occurred just prior to administration of the CDDP or saline (with or without a protective agent) and again 3 days later. All testing was performed with the animal in a double walled IAC booth.

Platinum/iridium needle electrodes were placed at the vertex (non-inverting) to a point directly below the ipsilateral pinna (inverting) with a ground electrode placed in the hind leg.

ABR data collection was obtained with a Biologic Traveler system with an additional custom made high frequency stimulator for 14000 Hz. ABR thresholds were measured in response to 100 microsecond clicks and for tonebursts with 1 ms rise/fall and 0 ms plateau gated by a Blackman envelope and centered at the frequencies of 1, 4, 8, and 14 kHz presented at 10/s. An intensity series was obtained for each animal from 100 to 0 dB peak equivalent SPL (peSPL) for click stimuli and Sound Pressure Level (SPL) for tonebursts in 10 dB decrements. The term peSPL means that the amplitude of the click stimulus from the prestimulus baseline to the first peak is equivalent to the SPL of a pure tone stimulus having the same prestimulus baseline to peak amplitude. Threshold was defined as the lowest intensity capable of eliciting a replicable, visually detectable response.

A total of 512 sweeps constituted each average. The recording epoch was 15 ms following stimulus onset. Responses were analogue filtered with a 30-3000 Hz bandpass.

Rectal temperature was monitored throughout recordings, with animal temperature being maintained by a warming pad.

Electron Microscopy

The animals were sacrificed by decapitation while under general anesthesia and cochleae perfused with fixative through the perilymphatic spaces. The primary fixative was 2.5% glutaraldehyde at 4° C. in 0.1M phosphate buffer (pH 7.4). A small hole in the otic capsule was hand drilled beneath the first turn with a three sided, sharpened pick. In vitro perfusion was performed intermittently within 5 minutes of sacrifice through the small hole in scala tympani, allowing the fluid to exit through the opened oval window. After perfusion fixation, the round window membrane was removed, and the cochleae were immersed in glutaraldehyde and stored in the refrigerator overnight.

After overnight fixation in glutaraldehyde, the cochleae were rinsed in 0.1 M phosphate buffer and gently perfused with the buffer through the perilymphatic spaces by loosely fitting the tube end of the perfusion syringe over the opening drilled in the scala tympani. Cochleae were then rinsed in buffer 3 times. After rinsing, the cochleae were post-fixed by a perfusion of 1.5% $OsO_4$ (at 4° C.) in phosphate buffer in a fume hood. Fixation was continued by immersion and rotation in the same fixative for 15 minutes. The cochleae were rinsed in the same fashion as after glutaraldehyde fixation.

Under the dissecting microscope, the bony capsule of the cochlea was carefully removed.

The tissue was then serially dehydrated in 2×50%, 70%, 85%, 95% and 3×100% ethanol. Each specimen was dried using Peldri and placed on a stub for sputter coating with 13 nm platinum. The tissue was viewed through a Hitachi S-500 scanning electron microscope and photographs taken on Polaroid type 55 land Film.

Semi-quantitative analysis per turn for the outer hair cells was performed in the following manner: For each turn of the cochlea, apical, middle, and base, a representative sample was examined. For each sample, 11 inner hair cells served as a guide to count a section of 33 outer hair cells or 11 per row. The number of damaged or missing outer hair cells within each sample was then counted.

Weight

Each animal's weight was measured in an Ohaus triple beam balance scale before administration of the anesthetic for the pretest and again before the post-test 3 days later.

Statistical Analysis

ABR data were analyzed using a three factor analysis of variance (ANOVA) with one between subject factor (groups) and two within subject factors (frequency and pre- vs. post-test). Each dependent variable was analyzed independently. Tests subsequent to the ANOVA were carried out in accordance with the Tukey HSD procedure. Weight loss and/or gastrointestinal protection was measured using the same type of statistical analysis as the ABR measures. SEM data were analyzed for each turn using a one way analysis of variance with Post-Hoc Tukey HSD analysis. The criterion for statistical significance for all measures was $p<0.01$.

Results

Hearing loss

Post test ABR hearing thresholds are presented in FIG. 1. As expected, no significant threshold shift in response to any stimulus occurred in the untreated control group, and marked significant threshold shift occurred in response to all stimuli, but particularly for the high frequencies, in the treated control group. For the animals receiving D-Met prior to the CDDP, 2/5 and 3/5 animals receiving 75 and 150 mg/kg D-Met, respectively, had complete otoprotection as defined by no significant ABR threshold shift for any stimulus. For the 300 mg/kg D-Met administration, all 5 animals had complete otoprotection for all stimulus conditions (FIG. 1). All experimental groups receiving any level of D-Met had significantly lower ABR thresholds than the treated control group for all stimuli, as did the untreated control group. This observed protection from hearing loss may occur not only as a result of protection of cochlear mechanisms, but also as a result of protection of the auditory neural pathway (i.e., neuroprotection).

Histology

Histologic findings (FIG. 2) were consistent with the ABR findings. All groups had essentially normal hair cell counts for the apical turn, with no significant difference between groups. For the middle and basal turns, only the treated control group showed significantly different findings from the untreated control group and from the three groups receiving preadministration of D-Met, with the basal turn being consistently more affected than the middle turn.

Weight Loss

Figure 3:
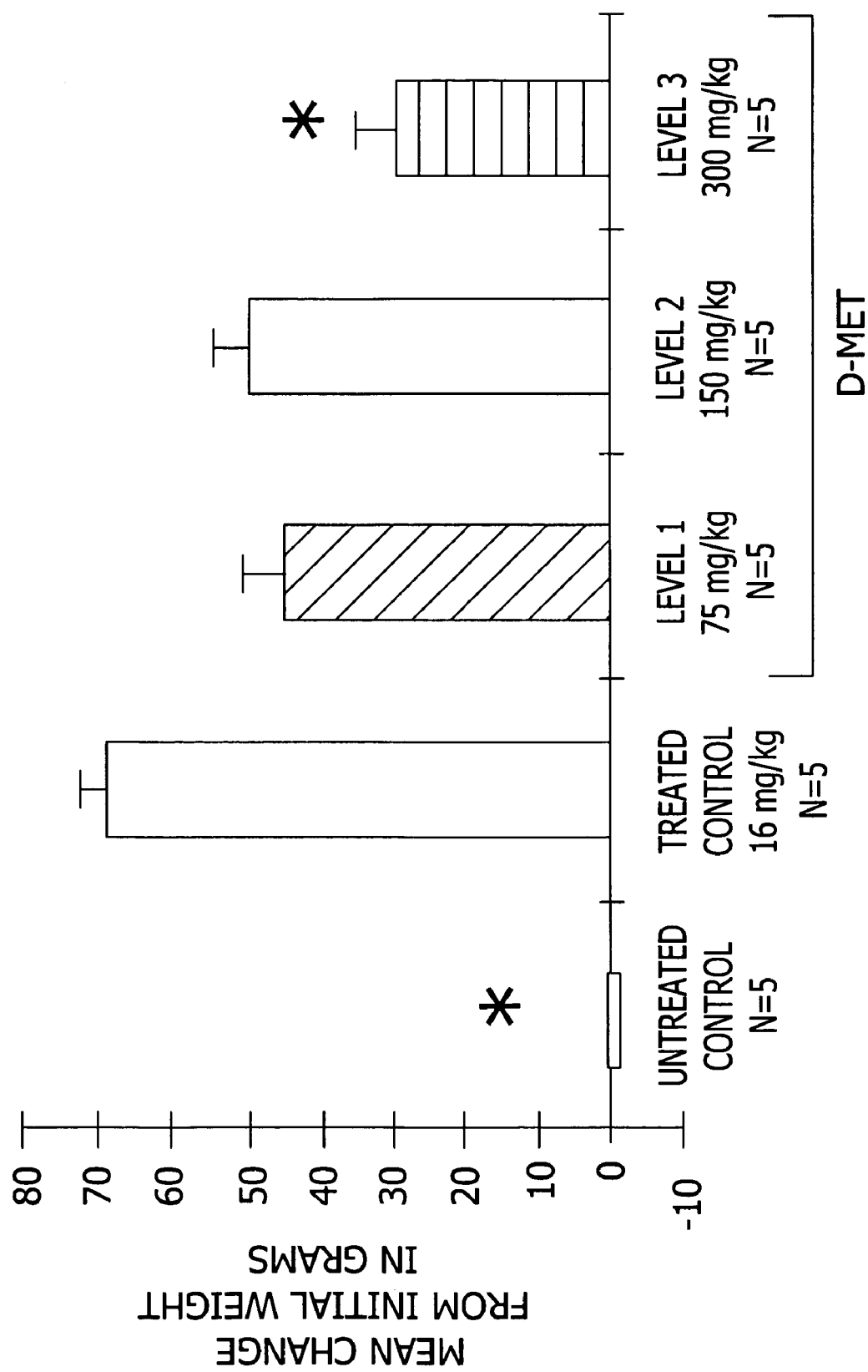
FIG. 3 shows the average weight loss in grams for the various animal groups. * indicates significantly different from the CDDP-treated controls at the $p \leq 0.1$ level.

CDDP-induced weight loss diminished as D-Met dosing increased (FIG. 3). Weight loss in the experimental group receiving 300 mg/kg was significantly less than that in the treated control group. The amount of weight loss across groups was significantly correlated with the amount of threshold shift for all stimuli, with the highest correlation for the 14 kHz stimulus.

Neuroprotection

Animals receiving D-Met were noticeably more lively, active, and coordinated on the morning of the third day as compared to the surviving treated control group animals.

Alopecia

The coats of animals receiving D-Met were noticeably superior to those of control group animals, and showed significantly less hair loss.

Survival During the Study Period

All 15/15 animals receiving any level of D-Met survived to the end of the study period as compared to 5/10 treated control group animals.

Discussion

The foregoing results demonstrate that 300 mg/kg D-Met administered 30 minutes before 16 mg/kg CDDP provides complete otoprotection, as indicated by ABR and histologic findings, while also reducing CDDP-induced weight loss, gastrointestinal toxicity, neurotoxicity, alopecia, and improving survival.

While not intending to be bound to any particular theory, I hypothesize that D-Met may provide these protective effects by any one or more of a number of different mechanisms.

According to Schweitzer, (1993), sulfur-containing compounds may prevent CDDP from interacting with intracellular target molecules, the nucleophilic oxygen or sulfur atoms interacting with the electrophilic site of the CDDP, thus displacing or extracting platinum after it is bound. Theoretically, these agents provide protection because of their high affinity for platinum complexes. It is known that CDDP reacts with methionine's sulfhydryl group (Lempers and Reedijk, 1990).

CDDP may preferentially bind to free D-Met, thus protecting glutathione. Reduced glutathione is an essential part of the anti-oxidant pathways. CDDP does reduce renal glutathione levels, resulting in increased lipid peroxidation (Hanneman and Baumann, 1988; Sugihara et al., 1987a, b; Boogaard, 1991). CDDP also reduces glutathione levels in the cochlea and inferior colliculus (Ravi et al., 1991). More recent work (Ravi et al., 1995, Rybak et al., 1995) investigated changes specifically in the cochlear antioxidant system. Systemic CDDP administration decreased reduced glutathione (GSH) levels, and reduced activity of the enzymes glutathione peroxidase (GSH-Px) and glutathione reductase (GR). Oxidized glutathione or glutathione disulfide (GSSG) was not found, suggesting that the overall glutathione levels decreased rather than merely being oxidized. Ravi et al., (1995) also reported increased cochlear malondialdehyde (MDA) levels, reflecting increased lipid peroxidation. Because CDDP does increase the level of free radicals in general (Hanneman and Baumann, 1988), preservation of the anti-oxidant system may be critical in preventing CDDP side effects.

D-Met preadministration may protect the sulfur groups of proteins, including protein bound L-methionine. CDDP binds to the methionine groups in protein and to glutathione (Lempers and Reedijk, 1990). Schweitzer, (1993) suggests that platinum binding to protein sulfhydryl groups may cause CDDP nephrotoxicity, accounting for the nephroprotective action of thiols (Gandara et al., 1989). It is logical that free D-Met may preferentially bind to CDDP because of the steric hindrance of the protein bound sulfur groups. This protection could occur by preferential binding of the CDDP to D-Met, or perhaps D-Met could reverse the Pt binding to the protein-bound methionine and glutathione, as do other sulfur-containing compounds (Lempers and Reedijk, 1990). Methionine can displace plasma-bound Pt (Alden and Repta, 1984).

D-Met binding to CDDP may also protect free L-methionine (L-Met), an essential amino acid. Parenteral administration of DL-methionine in humans results in higher plasma levels of the D- isomer (Printen et al., 1979). Because the D-Met is less well metabolized than L-Met in humans, it may remain more available for CDDP binding, thus protecting the L-Met for needed protein synthesis, cell activation, and metabolism.

Fortunately, D-Met does not inhibit CDDP anti-tumor action as determined against the Walker 256 carcinosarcoma in the rat (Jones and Basinger, 1989). Preadministration of methionine, presumably a racemic mixture, actually sensitized NHIK 3025 in vitro human uterine cervix carcinoma in situ cancer cells to CDDP cytotoxicity (Melvik and Petterson, 1987).

Several factors may account for D-Met's CDDP-protective action in nontumor cells as compared to tumor cells. Methionine metabolism is clearly different in tumor and nontumor cells (Hoffman, 1985), but how these differences may result in differential CDDP action has not been elucidated. The toxic effects of CDDP may also be different in tumor and nontumor cells. The CDDP anti-tumor effect results primarily from cisplatin's reaction with DNA, primarily at the N-7 bisguanine position. Initially, mono-adducts are formed, followed by rapid intra-strand cross-linking, causing cytotoxicity (see the review by Tognella, 1990). The binding of platinum to cytosolic ligands and nucleoprotein fractions may also play a role, but the receptors and interactions are not yet defined (Schweitzer, 1993). Significant DNA binding in normal cells is less likely because fewer DNA replication forks are open at any point in time, unlike in rapidly dividing tumor cells. In nontumor cells, the toxic effects may be largely secondary to the binding with amino acids, either free or protein-bound, and deactivation of the antioxidant pathway, as described above.

The timing of CDDP reactions may also be different in tumor and nontumor cells. CDDP uptake by the Walker 256 carcinosarcoma in the rat is very rapid, occurring in the first few minutes after administration, followed by a rapid redistribution that is complete within 15 minutes after injection (Jones and Basinger, 1989). Because the uptake of CDDP into tumor cells is very rapid, the binding to the DNA bisguanine groups, particularly at the open replication forks, may occur more rapidly than the reaction of CDDP with methionine.

Although CDDP uptake into the kidney is also rapid (Jones and Basinger, 1989), CDDP binding to protein is relatively slow. As reviewed by Schweitzer, (1993), following IV cisplatin administration, 90% of cisplatin is protein-bound within 2 hours, with half-lives of 25 to 50 minutes and 53 to 73 hours for unbound and bound platinum, respectively. Platinum tissue levels decline slowly. Platinum may still be measured over a week after high dosage administration, and bound fragments may still be present when the patient starts the next treatment cycle. Platinum uptake in the stria vascularis and the organ of Corti increases at least over a 24 hour period, which may underlie the dose-related cumulative ototoxicity (Schweitzer, 1993), but may also allow time for CDDP binding to D-Met before uptake into the cochlea.

However, the CDDP toxicities both in tumor and nontumor cells are complex, and many factors may be involved in D-Met's protective action.

A positive correlation between weight loss and outer hair cell loss in guinea pigs has been demonstrated (Tange et al., 1982, Hoeve et al., 1988), but both studies noted marked intersubject variability. The data presented above reveal a positive correlation between weight loss and threshold loss that increased as stimulus frequency increased. The significant reduction in weight loss with 300 mg/kg D-Met preadministration suggests that D-Met also alleviates some of the gastrointestinal toxicities of CDDP. The amelioration in weight loss by D-Met could also be related to a decrease in nephrotoxicity or other factors.

The elimination of CDDP mortality in this study by preadminstration of any of the three D-Met levels demonstrates a marked improvement in the overall health status of the animals. D-Met preadministration may therefore be useful in shifting the $LD_{50}$ level of CDDP and other platinum-containing anti-tumor agents, permitting the safe use of higher levels of these agents during chemotherapy, with potential improvement of the cancer cure rate.

Therapeutic Applications

The data presented above demonstrate that D-Met prevents CDDP-induced ototoxicity, reduces CDDP-induced weight loss, protects against CDDP-induced gastrointestinal toxicity, neurotoxicity, and alopecia, and improves survival during CDDP treatment in a mammal. Because CDDP-induced hearing loss in humans is almost invariably permanent, prevention of this hearing loss has a number of important consequences. If ototoxicity could be prevented, not only could hearing be spared, but perhaps higher doses of cisplatin and other platinum-containing antineoplastic agents could be routinely employed during chemotherapy, increasing the effectiveness of anti-tumor therapy in human patients.

The foregoing data also suggest that D-Met and the other methionine protective agents disclosed herein will be effective in the treatment of noise-induced, loop diuretic-induced, aminoglycoside antibiotic-induced, iron chelator-induced, quinine- and quinidine-induced, and radiation-induced ototoxicity, as well as in ameliorating other radiation-induced side effects such as neural damage, alopecia, gastrointestinal disorders, and in improving patient survival.

As used herein, the term "ototoxicity" includes, but is not limited to, any detrimental or pathologic change in the structure or function of the ear, including changes in hearing and balance. Auditory functional changes can include, but are not limited to, hearing loss or other changes in auditory threshold for any stimulus, perception of sound including recruitment (abnormal growth in the perception of loudness), ability to identify, localize, recognize, distinguish between, or process sounds, and/or distortion of sounds or any abnormality as measured by conventional auditory tests. This term also includes tinnitus (ringing or noises in the. ear), which includes any perception of sound that is not in response to an external signal. Further, ototoxicity includes any perceived or measured functional change in the balance or vestibular system, including, but not limited to, either induced or spontaneous vertigo, dysequilibrium, increased susceptibility to motion sickness, nausea, vomiting, nystagmus, syncope, lightheadedness, dizziness, difficulty in visual tracking secondary to vestibular or balance disorder or abnormality as measured on any test of vestibular or balance function. Structural changes can include any intra- or extra-cellular, multicellular, or organ change in the auditory or vestibular pathways from the external ear up through and including the cortex and all pathways in between.

The term "otoprotective agent" refers to an agent that prevents, ameliorates, or otherwise protects against ototoxicity.

The term "neurotoxicity" includes, but is not limited to, any detrimental or pathologic change in the structure or function in the neurologic system or any part thereof. Neurologic functional changes can include, but are not limited to, neuropathy, either central or distal, including a common "stocking and glove" pattern, tingling, loss of sensation, numbness, decreased vibratory sensation, decreased deep tendon reflexes, sensory ataxia, neuritis, focal encephalopathy, aphasia, autonomic neuropathy, postural hypotension, a myasthenia-like syndrome, muscle cramps, headache, seizures, blindness or visual disturbance secondary to disorder of the optic or visual neurological pathway, papilledema, hearing loss secondary to disorder of the auditory neurologic pathway, and/or loss of the sensation of taste. Structural changes can include intra- or extra-cellular, multicellular, or organ changes, anywhere in the neurologic system, including both peripheral and central systems. Neurotoxicity can manifest itself during or after the course of treatment with platinum-containing anti-tumor compounds.

The term "neuroprotective agent" refers to an agent that prevents, ameliorates, or otherwise protects against neurotoxicity.

The term "gastrointestinal toxicity" includes, but is not limited to, any detrimental or pathologic change in the structure or function in the gastrointestinal system or any part thereof. Gastrointestinal changes include, for example, current or delayed nausea, vomiting, esophageal reflux, stomatitis, bleeding along the gastrointestinal tract, diarrhea, weight loss, and/or anorexia. Gastrointestinal toxicity can manifest itself during or after the course of treatment with platinum-containing anti-tumor compounds.

The term "gastrointestinal-protective agent" refers to an agent that prevents, ameliorates, or otherwise protects against gastrointestinal toxicity.

In view of the results presented above, the medical or veterinary practitioner, by employing the compounds, compositions, and methods described below, will be able to maintain any of the foregoing parameters in a mammal, especially a human, at a level of from about 70% to about 80% of the pre-chemotherapy or other treatment or exposure level, more preferably from about 80% to about 90% of the pre-chemotherapy or other treatment or exposure level, most preferably from about 90% to about 100% of the pre-chemotherapy or other treatment or exposure level, as measured by standard tests routinely employed in the art. These compounds and methods can also be used for the treatment of domestic pets, such as cats and dogs.

The teachings presented herein permit the design of therapeutic regimens that can be employed to reduce the undesirable side effects of platinum-containing anti-tumor compounds such as CDDP, increase the dosing of such anti-tumor compounds to obtain a higher cancer cure rate, and perhaps include weaker patients in treatment protocols employing such anti-tumor compounds, from which they are currently excluded because they cannot withstand the toxicities associated therewith. The presently disclosed teachings also permit the design of therapeutic regimens useful in preventing or reducing the undesirable ototoxic side effects of noise, loop diuretics, aminoglycoside antibiotics, iron chelators, quinine, quinidine, and radiation, as well as other radiation-induced side effects such as neural damage, alopecia, gastrointestinal disorders, and decreased patient survival.

Administration of D-Met before, during, or after administration of antineoplastic effective amounts of platinum-containing anti-tumor compounds such as CDDP, or during various combinations of these time periods, is particularly useful in view of D-Met's lack of interference with CDDP anti-tumor action (Jones and Basinger, 1989; Melvik and Petterson, 1987).

D-Met and structurally related compounds can be used in conjunction with platinum-containing antitumor compounds such as CDDP during chemotherapy, and in conjunction with the use of loop diuretics, aminoglycoside antibiotics, iron chelators, quinine, and quinidine, as described below. These methionine protective agents can also be used to prevent or reduce the ototoxic effects of noise and radiation, as well as other radiation side effects, as described below as well.

Methionine and Its Derivatives

D-Met has been administered to humans for various purposes. For example, C-labeled D-Met has been used for radiographic imaging (Meyer et al., 1985), and DL-methionine has been administered for parenteral nutrition (Printen et al., 1979). D-Met has also been safely administered to humans orally for nutritional studies (Kaji et al., 1987; Kies et al., 1975; Stegink et al., 1986). Oral methionine is sold as an over the counter preparation to control urinary pH (Drug Facts and Comparisons, 1991). The contraindications are for patients with a history of liver disease, and that high dosage methionine may inhibit growth in children when given for an extended time period.

Analogs or derivatives of methionine useful in the present invention are compounds containing a methionine moiety, or a methionine-like moiety including a thioether group, that exhibit an otoprotectant effect, a weight-loss protectant effect, a gastrointestinal protectant effect, a neuroprotectant effect, an alopecia protectant effect, and/or a survival-enhancing effect when used in conjunction with an antitumor platinum coordination compound administered in an effective chemotherapeutic dose, a loop diuretic compound, an aminoglycoside antibiotic, an iron chelator, quinine, or in conjunction with exposure to noise or radiation. Among the compounds structurally related to D-Met that can be employed in the present invention are those containing the C—S—C— (thioether) moiety. These include, but are not limited to, compounds having the structural formula:

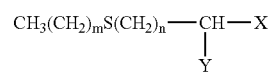

wherein m is an integer from 0 to 3; n is an integer from 1 to 3; $X = -OR^1, -OCOR^1, -COOR^1, -CHO, -CH(OR^1)_2$, or $-CH_2OH; Y = -NR^2R^3$ or $-OH; R^1 = H$ or a substituted or unsubstituted, straight, branched chain, or cyclic alkyl group having 1 to 6 carbon atoms, preferably 1 to 4 carbon atoms; $R^2 = H$ or a substituted or unsubstituted, straight or branched chain acyl group having 1 to 6 carbon atoms, preferably 1 to 4 carbon atoms; and $R^3 = H$ or a substituted or unsubstituted, straight or branched chain acyl group having 1 to 6 carbon atoms, preferably 1 to 4 carbon atoms; or a pharmaceutically acceptable salt thereof.

The lower alkyl and acyl groups described herein, either alone or containing the various substituents defined herein, can contain from one to six carbon atoms in the principal chain, and up to about 15 carbon atoms total. The lower alkyl groups include, for example, methyl, ethyl, propyl, isopropyl, butyl, hexyl, cyclopropyl, cyclopentyl, cyclohexyl, and the like. Substituents of the substituted alkyl and acyl groups described herein can include, for example, groups selected from alkyl, cycloalkyl, alkenyl, alkynyl, aryl, heteroaryl, O, S, N, P, or halogen (Cl, F, Br, or I) atoms. Optionally, these substituent alkyl, cycloalkyl, etc., groups can be substituted with O, S, N, P, or halogen (Cl, F, Br, or I) atoms. These substituent alkyl, cycloalkyl, etc., groups include, for example, lower alkoxy groups such as methoxy, ethoxy, and butoxy, and groups such as halo, nitro, amino, and keto.

The alkenyl groups described herein, either alone or with the various substituents defined herein, are preferably lower alkenyl containing from two to six carbon atoms in the principal chain, and up to about 15 carbon atoms total. They can be substituted, straight, or branched chain, and include ethenyl, propenyl, isopropenyl, butenyl, isobutenyl, hexenyl, and the like.

The alkynyl groups described herein, either alone or with the various substituents defined herein, are preferably lower alkynyl containing from two to six carbon atoms in the principal chain, and up to about 15 carbon atoms total. They can be substituted, straight or branched chain, and include ethynyl, propynyl, butynyl, isobutynyl, hexynyl, and the like.

The aryl moieties described herein, either alone or with various substituents defined herein, can contain from about 6 to about 15 carbon atoms, and include phenyl. Substituents include alkanoxy, protected hydroxy, halogen, alkyl, aryl, alkenyl, acyl, acyloxy, nitro, amino, amido, etc. Phenyl is a preferred aryl.

The heteroaryl moieties described herein, either alone or with various substituents defined herein, can contain from about 5 to about 15 atoms, and include, furyl, thienyl, pyridyl and the like. Substituents include alkanoxy, protected hydroxy, halogen, alkyl, aryl, alkenyl, acyl, acyloxy, nitro, amino, and amido.

The acyloxy groups described herein can contain alkyl, cycloalkyl, alkenyl, alkynyl, aryl, or heteroaryl groups.

The carbon atoms, i.e., the methyl and methylene groups, constituting the principal backbone of the methionine or methionine-like moiety can also be substituted as variously described above.

Non-limiting examples of such methionine protective agents include D-methionine (D-Met), L-methionine, a mixture of D-methionine and L-methionine, normethionine, homomethionine, methioninol, hydroxy methionine, ethionine, or pharmaceutically acceptable salts thereof. S-adenosyl-L-methionine, or a pharmaceutically acceptable salt thereof, can also be employed. Methionine protective agents of the present invention can be in the D-, L-, or DL- form, and include pharmaceutically acceptable N-(mono- and dicarboxylic acid) acyl derivatives and alkyl esters thereof. Exemplary acyl derivatives include the formyl, acetyl, propionyl, and succinyl derivatives. Exemplary ester derivatives include the methyl, ethyl, propyl, isopropyl, and butyl esters. D-Met is a preferred compound.

Collectively, methionine, along with the other compounds discussed above, can be referred to as "methionine protective agents." These compounds can be used alone or in various combinations with one another in the methods described herein.

These compounds can be administered alone, or in combination with the other drug compounds discussed herein, in the form of the water-soluble acid, free base, or as physiologically acceptable salts, including acid addition salts formed with organic and inorganic acids, for example, hydrochlorides, hydrobromides, sulfates, phosphates, citrates, fumarates, and maleates, and cations such as sodium, potassium, etc. These compounds can be formulated for administration to humans and animals with pharmaceutically acceptable carriers, excipients, and diluents, such as sterile distilled water, Ringer's solution, normal saline, 5% glucose, dextrose, fructose, sucrose, etc., and mixtures thereof, as is well known in the art. Antimicrobial agents, preservatives, etc., can also be included. Compositions for oral administration can include coloring and flavoring agents. Additional methods of formulating compounds of the present invention for administration in the methods described herein can be found, for example, in *Remington's Pharmaceutical Sciences*, Fifteenth Edition, Mack Publishing Company, Easton, Pa., 1975.

Anti-Tumor Platinum Compounds

Cisplatin (CDDP; cis-diamminedichloro-platinum(II)) is currently the anti-tumor platinum coordination compound most frequently employed in the therapy of testicular cancer, ovarian tumors, and a variety of other cancers. Methods of employing CDDP clinically are well known in the art (Nicolini, 1987). For example, CDDP can be administered in a single day over a six hour period, once per month, by slow intravenous infusion. For localized lesions, CDDP can be administered by local injection. Intraperitoneal infusion can also be employed. CDDP can be administered in doses as low as 10 mg/m$^2$ per treatment if part of a multi-drug regimen, or if the patient has an adverse reaction to higher dosing. At the low end, a more common clinical dose is about 30 mg/m$^2$; the high end of the range is about 120 to about 150 mg/m$^2$ per treatment. When used in conjunction with D-Met or other methionine protective agents, these dosages can be increased.

CDDP is representative of a broad class of water-soluble, platinum coordination compounds well known in the art that provide platinum in the form of an ion having anti-tumor activity. Among the anti-tumor platinum coordination compounds described in the literature which are useful in the methods of the present invention are, for example, trans-diaminedichloro-platinum(II), cis-diamine-diaquaplatinum (II)-ion, cis-diaminedichloroplatinum(II)-ion, chloro(diethylenetriamine)-platinum(II) chloride, dichloro (ethylenediamine)-platinum(II), diammine(1,1-cyclobutanedicarboxylato)-platinum(II) (carboplatin), spiroplatin, dichlorotrans-dihydroxybisisopropolamine platinum IV (iproplatin), diammine(2-ethylmalonato)-platinum(II), ethylenediamine-malonatoplatinum(II), aqua(1,2-diaminodiclohexane)-sulfatoplatinum(II), (1,2-diaminocyclohexane)malonato-platinum(II), (4-carboxyphthalato) (1,2-diaminocyclo-hexane)-platinum(II), (1,2-diaminocyclohexane)-(isocitrato)platinum(II), (1,2-diaminocyclohexane)-cis(pyruvato)platinum(II), and (1,2-diaminocyclohexane)-oxalatoplatinum(II).

Loop Diuretics

Loop diuretics are a group of compounds with dissimilar chemical structure, but which share a similar mechanism and site of action within the kidney: these compounds inhibit sodium chloride reabsorption at the high-capacity site in the thick ascending limb of the loop of Henle, causing greatly increased excretion of sodium chloride in the urine, and to a lesser extent of potassium. Loop diuretics are among the compounds exhibiting the greatest diuretic effect, and are commonly used in the treatment of edema of cardiac, hepatic, or renal origin. Use of these compounds can cause ototoxicity at least in part as a result of the alteration of electrolyte composition in the inner ear. In adults, ototoxicity is generally reversible, disappearing upon withdrawal of the drug; however, permanent hearing loss has been reported, particularly with ethacrynic acid. In neonates, reversibility of hearing loss may be permanent. Commonly used loop diuretics include, but are not limited to, furosemide (Lasix and other compounds), ethacrynic acid (Edecrin), bumetanide (Bumex and other compounds), piretanide, muzolimine, indapamide (Lozol), and xipamide. Loop diuretics greatly exacerbate the ototoxicity of platinum-containing antitumor compounds and aminoglycoside antibiotics. The interaction of these ototoxic compounds is synergistic; D-met and the other methionine protective agents disclosed herein may prevent their ototoxicity or ototoxic synergistic interaction.

Aminoglycoside Antibiotics

The aminoglycoside antibiotics share several structural features: they each contain one or more sugar moieties and a streptidine ring, and they each have one or more amino or guanidino groups. The currently available aminoglycoside antibiotics include streptomycin, kanamycin, gentamicin, amikacin, neomycin, netilmicin, paromomycin, vancomycin, hygromycin, erythromycin and tobramycin. One of the principal dangers associated with the use of aminoglycoside antibiotics is their ototoxicity, which is associated with either hearing loss (cochlear damage), vertigo (vestibular damage), or both. An early sign is tinnitus accompanied by loss of high-frequency hearing. Early detection of hearing loss can be reversed; prolonged treatment results in permanent hearing loss. The concomitant administration of other drugs that cause similar adverse effects potentiates the adverse effects of the aminoglycosides. Such other drugs include loop diuretic agents, as discussed above.

Iron Chelating Agents

Iron chelating agents such as deferoxamine mesylate (desferrioxamine mesylate; for example, Desferal) are used to treat patients exhibiting elevated levels of iron in the blood. Such patients include those suffering from sickle cell anemia, hereditary disorders resulting in elevated blood iron levels, those receiving frequent blood transfusions, those who have ingested large amounts of ferrous salts of iron (iron poisoning), etc. The use of iron chelating agents such as deferoxamine can result in ototoxicity.

Quinine and Quinidine

Quinine (Quinamm) has long been used as an antipyretic, analgesic, and antimalarial. Recently, it has been used to stabilize muscle membranes against repetitive activity. Specifically, it is used to treat myotonia congenita (Thomsen's disease) and nocturnal muscle cramp. Quinidine is a class IA antiarrhythmic agent useful in the treatment of atrial and ventricular arrhythmias.

The adverse side effects of quinine and quinidine are similar, and have been given the name "cinchonism," deriving from the fact that quinine is obtained from the bark of the cinchona tree. These side effects include disturbances of hearing, including tinnitus, deafness, and vertigo.

Noise

Noise-induced hearing loss, both impulse and chronic exposure, can damage hearing. In impulse noise, including blast exposure, the patient may suffer significant tympanic membrane and middle ear damage. In chronic exposure, which generally occurs at lower intensity levels, middle ear and tympanic membrane damage are unlikely. In noise exposure, the primary and initial damage is generally cochlear, with secondary neural degeneration of the auditory system occurring over time. Noise-induced hearing loss has been reviewed by the present inventor in the book entitled *Essential Audiology For Physicians* (1998) Singular Publishing Group, Inc., San Diego.

Noise-induced hearing loss can occur secondary to a single very loud noise exposure, or secondary to relatively high-level noise exposure over a long period of time. The risk of noise-induced hearing loss is related to both sound intensity and duration. Both the Occupational Safety and Health Administration (OSHA) and the Environmental Protection Agency (EPA) have established standards relevant to noise exposure levels in industry. The OSHA Permissible Noise Exposure Levels range from a duration of 32 hours at a sound level of 80 dBA to 0.25 hours at 115 dBA. For every 5 dB increase in the noise level, the allowable exposure duration is halved. Non-industrial, e.g., recreational, noises intense enough to damage hearing can vary, for example, from approximately 90 dBA (lawnmower) to approximately 140 dBA (shotgun blast).

Radiation

Exposure to radiation, whether intentional, as in radiation therapy, or unintentional, as by accident, war, etc., can result in ototoxicity, as well as neural damage (neurotoxicity), alopecia, gastrointestinal disorders, and reduced patient survival. Although physical rather than chemical, radiation can be considered another "ototoxin" in view of its toxicity to the ear and hearing. Radiation-induced hearing loss is more likely to involve the middle ear than is hearing loss caused by platinum-containing compounds or loop diuretics; however, cochlear and neural problems can also occur.

Radiation-induced ototoxicity, for example hearing loss, can occur as a result of exposure to 35-40 Gy or higher, either as a single or cumulative dose. Radiation-induced gastrointestinal toxicity, which is similar to that occurring during chemotherapy, includes electrolyte loss, secondary infections, bloody diarrhea, and gastrointestinal bleeding, and can occur upon exposure to a radiation dose in the range from 5-20 Gy, or higher.

Administration of Methionine Protective Agents

The methionine protective agents of the present invention can be administered orally or parenterally, for example intraperitoneally, by intravenous injection, intravenous infusion, etc., as described in *Remington's Pharmaceutical Sciences*, Fifteenth Edition, Mack Publishing Company, Easton, Pa., 1975. These protective agents can also be given by local administration, for example, when the platinum-containing chemotherapeutic agent is administered by local injection, as noted above. Localized administration of methionine protective agents can be carried out by topical application employing pharmaceutical formulations designed for this purpose as is known in the art, local injection, etc.

In one embodiment of the present invention, a methionine protective agent is administered topically to the round window membrane of the ear. Typically, such topical administration is carried out by applying a pharmaceutical formulation such as a topical solution comprising the otoprotective agent to the round window membrane by a micro-catheter or by injection into the middle ear. Suitable micro-catheters include those commercially available, for example, from IntraEar Corp., Denver, Colo. Preferably, the micro-catheter is attached to a battery-operated pump such as that commercially available from Disetronics, Inc., which is capable of automatically applying a topical solution comprising the otoprotective agent to the round window membrane, either continuously or intermittently.

Administration of the methionine protective agents of the present invention simultaneously with the administration of a platinum-containing chemotherapeutic agent, loop diuretic agent, aminoglycoside antibiotic, iron chelating agent, or quinine or quinidine, can be accomplished in several ways. For example, each agent can be formulated individually and administered separately at the same time via any of the routes described herein or which are otherwise conventional in the art. Alternatively, both can be contained together in a single dose formulation that can be administered by a single route. As in the case of the platinum-containing chemotherapeutic agent, loop diuretic agent, etc., the dose of methionine protective agent can be administered in a single day.

Dosages

The methionine protective agents discussed above can be employed in methods for treating human and animal patients undergoing treatment with anti-cancer effective amounts of platinum-containing chemotherapeutic agents to prevent or reduce ototoxicity, weight loss, gastrointestinal toxicity, neurotoxicity, alopecia, and to prolong survival. In addition, these methionine protective agents can be employed in methods for treating human and animal patients undergoing treatment with diuretic-effective amounts of loop diuretic agents, antibiotic-effective amounts of aminoglycoside antibiotics, iron chelating-effective amounts of iron chelating agents, effective amounts of quinine or quinidine, or in methods for treating human and animal patients exposed to ototoxic noise levels, and methods for treating human and animal patients exposed to radiation levels capable of causing ototoxic effects such as hearing loss, as well as radiation-induced neural damage, alopecia, and gastrointestinal disorders. The present methionine protective agents can also improve survival in patients exposed to radiation.

These methods comprise administering to the patient an appropriate effective amount of a methionine protective agent prior to, simultaneously with, or subsequent to administration of a platinum-containing chemotherapeutic agent, loop diuretic agent, aminoglycoside antibiotic, iron chelating agent, or quinine or quinidine, or exposure of the patient to noise or radiation. Combinations of these time periods can also be employed.

Typically, the methionine protective agents of the present invention can be administered orally; parenterally by intravenous injection or slow infusion; intraperitoneally; or topically by application to the round window membrane of the ear. When administered parenterally, the effective amount of methionine protective agent can be in the range of from about 1.0 mg/kg body weight to about 600 mg/kg body weight. More preferably, the effective amount of methionine protective agent ranges from about 5 mg/kg body weight to about 500 mg/kg body weight, even more preferably from about 10 mg/kg body weight to about 400 mg/kg body weight.

Alternatively, the effective amount of methionine protective agent can be expressed on a mole:mole basis in relation to the anti-cancer effective amount of platinum-containing chemotherapeutic agent. This effective amount can be in the range of from about 4:1 to about 167:1, more preferably from about 4.25:1 to about 100:1, and most preferably from about 4.68:1 to about 20:1, methionine protective agent:platinum-containing chemotherapeutic agent, on a molar basis. A dosing ratio of about 18.75:1 on a molar basis is a preferred ratio.

If necessary, the amounts and ratios described above can be modified for different platinum-containing chemotherapeutic agents, loop diuretic agents, aminoglycoside antibiotics, iron chelating agents, and quinine or quinidine, or exposure to noise and radiation, by routine optimization, including monitoring of effectiveness and titration for the desired effect, by the methods described herein.

When administered orally, the methionine protective agent should be given in an amount that will result in a blood serum level equivalent to that achieved by the parenterally administered dosages set forth above. Such effective oral dosages can easily be determined by one of ordinary skill in the art via conventional in vitro or in vivo methods such as those described in *Remington's Pharmaceutical Sciences*, Fifteenth Edition, Mack Publishing Company, Easton, Pa., 1975.

When administered topically to the round window membrane of the ear, the effective amount of otoprotective agent is typically administered as a pharmaceutical formulation such as a topical solution. Generally, topical administration comprises applying from about 0.001 ml to about 0.010 ml, preferably from about 0.0025 ml to about 0.0075 ml, and most preferably about 0.005 ml of a topical solution comprising the otoprotective agent to the round window membrane. The topical solution typically comprises from about 10 mg/ml to about 50 mg/ml, preferably from about 20 mg/ml to about 30 mg/ml, and most preferably about 25 mg/ml of otoprotective agent.

Treatment Regimen

In the various methods of the present invention, the effective amount of sulfur-containing protective agent can be administered prior to, contemporaneously with, or subsequent to administration of the effective amount of platinum-containing chemotherapeutic agent, loop diuretic agent, aminoglycoside antibiotic, iron chelating agent, or quinine or quinidine, or exposure of the patient to harmful noise or radiation. Combinations of these time periods can also be employed. Generally, prior administration of the effective amount of the otoprotective agent can be conducted broadly within the period ranging from as much as 14 days (i.e., about 336 hours, about 168 hours, about 84 hours or about 60 hours or less) before administration of the platinum-containing chemotherapeutic agent, loop diuretic agent, etc., or exposure to noise or radiation. Likewise, subsequent administration of the effective amount of the otoprotective agent can be conducted broadly within the period including as much as 14 days (i.e., including about 60 hours, about 84 hours, about 168 hours or about 336 hours or more) after administration of the platinum-containing chemotherapeutic agent, loop diuretic agent, etc., or exposure to noise or radiation.

Preferably, prior administration of the effective amount of the methionine protective agent is within about 48 hours before administration of the platinum-containing chemotherapeutic agent, loop diuretic agent, etc., or exposure to noise or radiation; with subsequent administration within about 48 hours after administration of the platinum-containing chemotherapeutic agent, loop diuretic agent, etc., or exposure to noise or radiation. More preferably, prior administration can be within about 36 hours before administration of the platinum-containing chemotherapeutic agent, loop diuretic agent, etc., or exposure to noise or radiation; and subsequent administration can be within about 36 hours after administration of the platinum-containing chemotherapeutic agent, loop diuretic agent, etc., or exposure to noise or radiation. Still more preferably, prior administration can be within about 25 hours before, and subsequent administration can be within about 25 hours after, administration of the platinum-containing chemotherapeutic agent, loop diuretic agent, etc., or exposure to harmful levels of noise or radiation. Even more preferably, prior administration can be within about 6 hours before, and subsequent administration can be within about 1 hour after, administration of the platinum-containing chemotherapeutic agent, loop diuretic agent, etc., or exposure to noise or radiation. Even more preferably, prior administration of the effective amount of methionine protective agent can be within about 1 hour before, and subsequent administration can be within about 1 hour after, administration of the platinum-containing chemotherapeutic agent, loop diuretic agent, etc., or exposure to noise or radiation. Still more preferably, prior administration of the effective amount of methionine protective agent can be within about one-half hour before, and subsequent administration can be within about one-half hour after, administration of the platinum-containing chemotherapeutic agent, loop diuretic agent, etc., or exposure to noise or radiation.

The platinum-containing chemotherapeutic agent can be administered parenterally, for example by slow intravenous infusion, or by local injection, as discussed above. Loop diuretic agents can be administered orally or parenterally, for example by slow intravenous infusion or by local injection, as is well known in the art. Aminoglycoside antibiotics, iron chelating agents, quinine, quinidine, and radiation can also be administered by routes and in doses conventional in the art. The methionine protective agent can be administered orally, parenterally by intravenous injection or slow infusion, intraperitoneally or topically to the round window membrane.

In a preferred embodiment of the present invention, when treating or preventing otoxicity due to exposure to noise, the effective amount of the otoprotective agent can be administered prior to, simultaneously with, or subsequently to the noise exposure. For example, it has been found that administering the otoprotective agent twice daily for a period ranging from about 14 days (i.e., from about 336, 168, 84, or 60 hours or less) before the noise exposure to about 14 days (i.e., from up to about 60, 84, 168, or 336 hours) after the noise exposure, preferably from about 7 days before the exposure to noise to about 7 days after the exposure to noise, and more preferably from about 48 hours before the exposure to noise to about 48 hours after the exposure to noise (i.e., from about 36, 24, 12, 6, 4, 2, 1 or ½ hour before to about ½, 1, 2, 4, 6, 12, 24 or 36 hours after the exposure to noise), can significantly ameliorate or prevent ototoxicity in a human or animal patient.

When the otoprotective agent is administered to the round window membrane, the otoprotective agent may be administered continuously or periodically during any of the time periods described above by introducing a topical solution into the ear as described above, i.e., by administration with a micro-catheter or by injection into the middle ear, preferably by administration with a micro-catheter equipped with an automatic, battery-operated pump.

Delayed toxic effects due to platinum-containing chemotherapeutic agents have been observed. The protective effects of the present methionine protective agents can be enhanced by administering them in a supplemental manner during the course of the patient's chemotherapy and/or afterwards as necessary or as desired. The same considerations apply in the case of loop diuretics, aminoglycoside antibiotics, iron chelating agents, quinine, quinidine, noise-induced hearing damage, and radiation exposure. Thus, the methods described herein can further comprise semi-daily, daily or weekly administration of a supplemental amount of methionine protective agent.

Stated another way, it is often beneficial to administer supplemental doses of the otoprotective agents of the present invention so as to maintain effective blood serum levels of the otoprotective agents. Generally, the administration of supplemental amounts of otoprotective agents should result in the blood serum level of the human or animal patient being maintained within at least about 10%, preferably from about 20% to about 70%, and more preferably within about 40%, of the blood serum level of the patient that results from the administration of the effective amount of otoprotective agent. Typically, such supplemental doses are administered within the time frames and dosages set forth above for the effective amount of otoprotective agents, for example, semi-daily, daily or weekly for a period of from about one to fourteen days after the administration of the effective amount.

As with the effective amount of methionine protective agent described above, the supplemental methionine protective agent can be administered orally; parenterally by intravenous injection or slow infusion; intraperitoneally or topically by application to the round window membrane. When administered parenterally, the supplemental amount of the methionine protective agent is preferably in the range of from about 1.0 mg/kg body weight to about 600 mg/kg body weight, more preferably from about 5 mg/kg body weight to about 500 mg/kg body weight, even more preferably from about 10 mg/kg body weight to about 400 mg/kg body weight.

Alternatively, the supplemental amount of methionine protective agent parenterally administered daily or weekly can be expressed on a mole:mole basis in relation to the anti-cancer effective amount of platinum-containing chemotherapeutic agent. This effective amount can be in the range of from about 4:1 to about 167:1, more preferably from about 4.25:1 to about 100:1, and most preferably from about 4.68:1 to about 20:1, methionine protective agent:platinum-containing chemotherapeutic agent, on a molar basis. A dosing ratio of about 18.75:1 on a molar basis is preferred.

Oral or parenteral doses administered daily can be within the lower ranges listed above. When administered orally, daily or weekly doses should be designed to achieve serum levels equivalent to those achieved by administration of the various parenteral doses described above.

When administered topically to the round window membrane, the supplemental amount of otoprotective agent may be administered in the same way as described above for the effective amount, typically as a pharmaceutical formulation such as a topical solution. Generally, the supplemental topical administration comprises applying from about 0.001 ml to about 0.010 ml, preferably from about 0.0025 ml to about 0.0075 ml, and most preferably about 0.005 ml of a topical solution comprising the otoprotective agent to the round window membrane. The topical solution typically comprises from about 10 mg/ml to about 50 mg/ml, preferably from about 20 mg/ml to about 30 mg/ml, and most preferably about 25 mg/ml of otoprotective agent.

Optimization of Treatment Regimen

In the methods of preventing or reducing ototoxicity of the present invention, various parameters associated with the patient's hearing and vestibular systems can be tested by methods well known in the art to establish pretreatment baseline values. After administration of the methionine protective agent, and over the course of chemotherapy and afterwards, ototoxic effects can be monitored by conventional tests, and the results can be compared to those obtained prior to treatment to determine if any change has occurred. If any impairment is observed, the amount and/or time of administration of the protective agent administered in conjunction with subsequent doses of the platinum-containing chemotherapeutic agent, loop diuretic agent, aminoglycoside antibiotic, iron chelating agent, quinine, quinidine, or exposure to noise or radiation, can be adjusted so as to reduce or prevent further ototoxic changes without substantially diminishing the antineoplastic effectiveness of the platinum-containing chemotherapeutic agent or radiation, the diuretic effect of the loop diuretic agent, etc. Similar modification of treatment parameters in the case of weight loss, gastrointestinal toxicity due to either the platinum-containing chemotherapeutic agent or radiation, neurotoxicity due to either the platinum-containing chemotherapeutic agent or radiation, alopecia due to either the platinum-containing chemotherapeutic agent or radiation, and overall patient condition/survival due to either the platinum-containing chemotherapeutic agent or radiation can be employed to optimize the protective effects of the protective agent with respect thereto. This can be achieved via appropriate testing and comparison of pre- and post-treatment values, e.g., patient weight and patient physical/medical/physiological condition, etc., with protocol adjustments being made as needed.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

BIBLIOGRAPHY

Aamdal, S., Fodstad, O., and Pihl, A. (1987) Some Procedures to Reduce Cis-platinum Toxicity Reduce Antitumour Activity. Cancer Treat. Rev. 14, 389-395.

Aguilar-Markulis, N. V., Beckley, S., Priore, R., and Mettlin, C. (1981) Auditory Toxicity Effects of Long-Term Cis- Dichlorodiammineplatinum II Therapy in Genitourinary Cancer Patients. J. Surg. Oncol. 16, 111-123.

Alden, W. W. and Repta, A. J. (1984) Exacerbation of Cisplatin-Induced Nephrotoxicity by Methionine. Chem. Biol. Interact. 48 (1), 121-124.

Anderson, M. E., Naganuma, A., and Meister, A. (1990) Protection Against Cisplatin Toxicity by Administration of Glutathione Ester. FASEB J. 4, 3251-3255.

Anniko, M., and Sobin, A., (1986) Cisplatin: Evaluation of Its Ototoxic Potential. Am. J. Otol. 7, 276-293.

Argov, Z. and Mastaglia, F. L. (1979) Drug Therapy: Disorders of Neuromuscular Transmission Caused by Drugs. New. Engl. J. Med. 301(8), 409-13.

Bajorin, D., Bosl, G. J., and Fein, R. (1987) Phase I Trial of Escalating Doses of Cisplatin in Hypertonic Saline. J. Clin. Oncol. 5(10), 1589-1593.

Berry, J. M., Jacobs, C., Sikic, B., Halsey, J., and Borch, R. F. (1990) Modification of Cisplatin Toxicity With Diethyldithiocarbamate. J. Clin. Oncol. 8(9), 1585-1590.

Berry, J. M., Sikic, B. I., Halsey, J., and Jacobs, C. D. (1989) A Phase 1 Trial of Diethyldithiocarbamate (DDTC) As a Modifier of Cisplatin (CP) Toxicity. Proceedings of ASCO, (266) 8, 69.

Blumenreich, M. S., Woodcock, T. M., Jones, M., Richman, S. P., Gentile, P. S., Kubota, T. T., and Allegra, J. C. (1985) High-Dose Cisplatin in Patients With Advanced Malignancies. Cancer 55, 1118-1122.

Boogaard, P. J., Slikkerveer, A., Nagelkerke, J. F., and Mulder, G. J. (1991) The Role of Metallothionein in the Reduction of Cisplatin-induced Nephrotoxicity by $Bi^{3+}$-Pretreatment in the Rat In Vivo and In Vitro. Biochem. Pharmacol. 41(3), 369-375.

Borch, R. F., Dedon, P. C., and Montine T. J. (1988) Experimental Approaches to Reducing Platinum Induced Kidney Toxicity. Hacker, M. P., Lazo, J. S., Tritton, T. R. (Eds) Organ Directed Toxicities of Anticancer Drugs, Matinus Nijhoff Publishing, pp. 190-20. (iii)

Campbell, K. C. M., Rybak, L. P., Meech, R. P., and Hughes, L. (1996) D-Methionine Provides Complete Protection from Cisplatin Ototoxicity in the Rat. Hearing Research 102, 90-98.

Church, M. W., Kaltenbach, J. A., Blakely, B. W., and Burgio, D. L., (1995) The Comparative Effects of Sodium Thiosulfate, Diethylcarbamate, Fosfomycin, and WR-2721 on Ameliorating Cisplatin-induced Ototoxicity. Hear. Res. 86(1,2), 195-203

Dedon, P. C., and Borch, R. F. (1984) Diethyldithiocarbamate (DDTC) Reversal of Cisplatin (DDP) Nephrotoxicity. AACR Abstracts, (1470) p. 371.

Deegan, P. M., Pratt, I. S., and Ryan, M. P. (1994) The Nephrotoxicity, Cytotoxicity and Renal Handling of a Cisplatin-Methionine Complex in Male Wistar Rats. Toxicology 89, 1-14.

Drug Facts and Comparisons (1991) Olin, B., Hebel, S. K. Connell, S. I., Dombek, C. E., Kastrup, E. K. (Eds.) J. P Lippincott Company, St. Louis, pg. 2115. (iii)

Endresen, L., Schjerven, L., and Rugstad, H. E. (1984) Tumours From a Cell Strain with a High Content of Metallothionein Show Enhanced Resistance Against cis-dichlorodiammineplatinum. Acta Pharmacol. Toxicol. 55(3), 183-187.

Estrem, S. A., Babin, R. W., Ryu, J. H. and Moore, K. C. (1981) Cis-Diamminedichloroplatinum (II) Ototoxicity in the Guinea Pig. Otolaryngol. Head Neck Surg. 89, 638-745.

Fausti, S. A., Schechter, M. A., Rappport, B. Z., and Frey, R. H. (1984) Early Detection of Cisplatin Ototoxicity. Selected Case Reports. Cancer 53, 224-231.

Fillastre, J. P. and Raguenez-Viotte (1989) Cisplatin Nephrotoxicity. Toxicol. Lett. 46, 163-175.

Fleischman, R. W., Stadnicki, S. W., Ethier, M. F. and Schaeppi, U. (1975) Ototoxicity of Cis-Dichlorodiammine Platinum (II) in the Guinea Pig. Toxicol. Appl. Pharmacol. 33, 320-332.

Forastiere, A. A., Takasugi, B. J., Baker, S. R., Wolf, G. T., and Kudla-Hatch, V. (1987) High-dose Cisplatin in Advanced Head and Neck Cancer. Cancer Chemother. Pharmacol. 19, 155-158.

Gandara, D. R., Perez, E. A., Lawrence, H. J., Degregorio, M. W., Martinez, C. A. (1989a) Phase I Trial of High Dose Cisplatin Plus Diethyldithiocarbamate Rescue: Toxicity Profile Compared to Patients Receiving High Dose Cisplatin Alone. Proc. Am. Assoc. Cancer Res. (959), Vol. 30, p. 241.

Gandara, D. R., Perez, E. A., Phillips, W. A., Lawrence, H. J., and DeGregoria, M. (1989b) Evaluation of Cisplatin Dose Intensity: Current Status and Future Prospects. Anticancer Res. 9, 1121-1128.

Gandara, D. R. et al. (1990) Crit. Rev. Oncol. Hematol. 10, 353-365.

Gandara, D. R., Perez, E. A., Wiebe, V., and DeGregio, M. W. (1991) Cisplatin Chemoprotection and Rescue: Pharmacologic Modulation of Toxicity. Sem. Oncol. 18(1), 49-55.

Glover, D., Glick, J.H., Weiler, C., Fox, K., and Guerry, D. (1987) WR-2721 and High Dose Cisplatin: An Active Combination in the Treatment of Metastatic Melanoma.

J. Clin. Oncol. 5, 574-578.

Griffin, J. P., (1988) Review Article: Drug-induced Ototoxicity. Br. J. Audiol. 22, 195-210.

Hacker, M. P. (1991) Toxicity of Platinum-Based Anticancer Drugs. Powis, G., & Hacker, M.P. (Eds) The Toxicity of Anticancer Drugs, Pergamon Press, pp. 82-105. (ii).

Hannemann, J., and Baumannn, K. (1988) Cisplatin-induced Lipid. Peroxidation and Decrease of Gluconeogenesis in Rat Kidney Cortex: Different Effects of Antioxidants and Radical Scavengers. Toxicology 51, 119-132.

Hoeve, L. J., Mertens zur Borg, I. R. A. M., Rodenburg, M., Brocaar, M. P., and Groen, B. G. S. (1988) Correlations between Cis-Platinum Dosage and Toxicity in a Guinea Pig Model. Arch. Otorhinolaryngol. 245, 98-102.

Hoffman, R. M., Altered Methionine Metabolism and Transmethylation in Cancer. Anticancer Res. 5, 1-30.

Howell, S. B., Pfeifle, C. L., Wung, W. E., Olshen, R. A., Lucas, W. E., Yon, J. L., and Green, M. (1982) Ann. Int. Med. 97(6), 845-851.

Jones, M. M., and Basinger, M. A. (1989) Thiol and Thioether Suppression of Cis-Platinum-Induced Nephrotoxicity in Rats Bearing the Walker 256 Carcinosarcoma. Anticancer Res. 9, 1937-1942.

Jones, M. M., Basinger, M. A., Mitchell, W. M., and Bradley, C. A. (1986) Inhibition of Cis-Diamminedichloroplatinum (II)—Induced Renal Toxicity in the Rat. Cancer Chemother. Pharmacol. 17, 38-42.

Jones, M. M., Basinger, M. A., and Holscher, M. A. (1991a) Relative Effectiveness of some Compounds for the Control of Cisplatin-Induced Nephrotoxicity. Toxicology 68, 227-247.

Jones, M. M., Basinger, M. A., and Holscher, M. A. (1991b) Thioether Suppression of Cisplatin Nephrotoxicity in the Rat. Anticancer Res. 11, 449-454.

Jones, M. M., Basinger, M. A., Field L., and Holscher, M. A. (1991c) Coadministration of Ditnethyl Sulfoxide Reduces Cisplatin Nephrotoxicity. Anticancer Res. 11, 1939-1942.

Jones, M. M., Basinger, M. A., and Holscher, M. A. (1992) Control of the Nephrotoxicity of Cisplatin by Clinically Used Sulfur-Containing Compounds. Fundam. Appl. Toxicol. 18, 181-188.

Kaji, H., Niioka, T., Kojima, Y., Yoshida, Y., and Kawakami, Y. (1987) Urinary 3-Methylthiopropionate Excretion and the Effect of D- or L-Methionine Ingestion Studied in Healthy Subjects. Res. Commun. Chem. Pathol. Pharmacol. 36 (1), 101-109.

Kies, C., Fox, H., and Aprahamian, S. (1975) Comparative Value of L-, DL-, and D-Methionine Supplementation of an Oat-based Diet in Humans. J. Nutr. 105, 809-814.

Koegel, L. (1985) A Contemporary Review of Aminoglycosides, Loop Diuretics, Acetylsalicylic Acid, Quinine, Erthromycin, and Cisplatinum. Am. J. Otol. 6(2), 190-199.

Komune, S. (1981) Potentiating Effects of Cisplatin and Ethacrynic Acid in Ototoxicity. Arch. Otolaryngol. 101, 66-74.

Kopelman, J., Budnick, A. S., Kramer, M. B., Sessions, R. B., and Wong, G. Y. (1988) Ototoxicity of High-Dose Cisplatin by Bolus Administration in Patients with Advanced Cancers and Normal Hearing. Laryngoscope 98, 858-864.

Laurell, G., and Engström, B. (1989) The Ototoxic Effect of Cisplatin on Guinea Pigs in Relation to Dosage. Hear. Res. 38, 27-34.

Lempers, E. L. M., and Reedijk, J. (1990) Reversibility of Cisplatin-Methionine in Proteins by Diethyldithiocarbamate or Thiourea: A study with Model Adducts. Inorgan. Chem. 29, 217-222.

Lippman, A. J., Helson, C., Helson, L., and Krakoff, I. H. (1973) Clinical Trials of Cis-Diamminedichloroplatinum (NSC-119875). Cancer Chemother. Rep. Part 1 57, 191-200.

Markman, M., Cleary, S., Pfeifle, C. E., and Howell, S. B. (1985) High-dose Intracavitary Cisplatin With Intravenous Thiosulphate: Low Incidence of Serious Neurotoxicity. Cancer 56, 2364-2368.

Melamed, A. B., Selim, M. A., Facog, Facs, and Schuchman, D. (1985) Cisplatin Ototoxicity in Gynecologic Cancer Patients. A Preliminary Report. Cancer 55, 41-43.

Melvik, J. E. and Petterson, E. O. (1987) Reduction of Cis-Dichlorodiammineplatinum-Induced Cell Inactivation by Methionine. Inorganica Chimica Acta 137, 115-118.

Meyer, G. J., Schober, O. and Hundeshagen, H. (1985) Uptake of $^{11}$C-L- and D-Methionine in Brain Tumors. Eur. J. Nucl. Med. 10, 373-376.

Meyer, W. H. (1989) Hearing Loss in Children and Young Adults Receiving Cisplatin With or Without Prior Cranial Irradiation. J. Clin. Oncol. 7(6), 754-760.

Mollman, J. E., Glover, D. J., Hogan, W. M., and Furman, R. E. (1988) Cisplatin Neuropathy—Risk Factors, Prognosis, and Protection by WR-2721. Cancer 61, 2192-2195.

Moroso, M. J., and Blair, R. L. (1983) A Review of Cis-Platinum Ototoxicity. J. Otolaryngol. 12(6), 365-369.

Naganuma, A., Satoh, M., and Imura, N. (1987) Prevention of Lethal and Renal Toxicity of Cis-diamminedichloroplatinum(II) by Induction of Metallothionein Synthesis Without Compromising Its Antitumor Activity in Mice. Cancer Res. 47, 983-987.

Nakano, S., and Gemba, M. (1989) Potentiation of Cisplatin-Induced Lipid Peroxidation in Kidney Cortical Slices by Butathione Depletion. Jpn. J. Pharmacol. 50, 87-92.

Nicolini, M. (Ed.) (1987) Platinum and Other Metal Coordination Compounds in Cancer Chemotherapy. Proceedings of the 5th International Syumposium on Platinum and Other Metal Coordination Compounds in Cancer Chemotherapy, Padua, Italy, June 29-Jul. 2, 1987. Martincis Nijhoff Publishing, Boston.

Otto, W. C., Brown, R. D., Gage-White, L. Kupetz, S., Anniko, M., Penny, J. E., and Henley, C. M. (1988). Effects of Cisplatin and Thiosulfate Upon Auditory Brainstem Responses of Guinea Pigs. Hear. Res. 35, 79-86.

Ozols, R. F., and Young, R. C. (1985) High-Dose Cisplatin Therapy in Ovarian Cancer. Semin. Oncol. 12(4), Suppl. 6, 21-30.

Paredes, J., Hong, W. K., Felder, T. B., Dimery, I. W., Choksi, A. J., Newman, R. A., Castellanos, A. M., Robbins, K. T., McCarthy, K., Atkinson, Kramer, A. M., Hersh, E. M., and Goepfert, H. (1988) Prospective Randomized Trial of High-dose Cisplatin and Fluorouracil Infusion With or Without Sodium Diethyldithiocarbamate in Recurrent and/or Metastatic Squamous Cell Carcinoma of the Head and Neck. J. Clin. Oncol. 6, 955.

Pfeifle, C. E., Howell, S. B., Felthouse, R. D., Woliver, T. B. S., Andrews, P. S., Markman, M., and Murphy, M. P. (1985) High-Dose Cisplatin With Sodium Thiosulfate Protection. J. Clin. Oncol. 3, 237-244.

Pollera, C. F., Marolla, P., Nardi, M., Ameglio, F., Cozzo, L., and Bevere, F. (1988) Very High-Dose Cisplatin-Induced Ototoxicity: A Preliminary Report on Early and Long-Term Effects. Cancer Chemother. Pharmacol. 21, 61-64.

Printen, K. J., Brummel, M. C., Ei Soon Cho, M. S. and Stegink, L. D. (1979) Utilization of D-Methionine During Total Parenteral Nutrition in Postsurgical Patients. Am. J._Clin. Nutr. 32, 1200-1205.

Qazi, R., Chang, A. Y. C., Borch, R. F., Montine, T., Dedon, P., Loughner, J., and Bennett, J. M. (1988) Phase I Clinical and Pharmacokinetic Study of Diethyldithiocarbamate as a Chemoprotector From Toxic Effects of Cisplatin. J. Natl. Cancer Inst. 80(18), 1486-1492.

Ravi, R., Rybak, L. P., and Somani, S. M. (1991) Relationship of Pharmacodynamic Effects of Cisplatin to the Glutathione Levels in Cochlea, Inferion Colliculus and Kidney. Pharmacologist 33(3), 217.

Ravi, R., Rybak, L. P., Hoffman, D., Whitworth, C., and Scott, V. (1992) Diethyldithiocarbamate Protects Against Cisplatin Ototoxicity and Nephrotoxicity. Otolaryngol. Head Neck Surg. 107(2), 232.

Ravi, R. Somani, S. and Rybak, L. (1995) Mechanism of Cisplatin Ototoxicity: Antioxidant System. Pharmacol. Toxicol. 76, 386-394.

Rothenberg, M. L., Ostchega, Y., Steinberg, S. M., Young, R. C., Hummel, S. and Ozols, R. F. (1988) High-Dose Carboplatin with Diethyldithiocarbamate Chemoprotection in Treatment of Women with Relapsed Ovarian Cancer. J. Natl. Cancer Inst. 80, 1488-1492.

Rubin, J. S., Wadler, S., Beitler, J. J., Haynes, H., Rozenblit, A., McGill, F., Goldberg, G., and Runowicz, C. (1995) Audiological Findings in a Phase I Protocol Investigating the Effect of WR2721, High-Dose Cisplatin and Radiation Therapy in Patients with Locally Advanced Cervical Carcinoma. J. Laryngol. Otol. 109(8), 744-747.

Rybak, L. P, Ravi, R. and Somani, S. (1995) Mechanism of Protection by Diethyldithiocarbamate Against Cisplatin Ototoxicity: Antioxidant System. Fundam. Appl. Toxicol. 26, 293-300.

Satoh, M., Kloth, D. M., Kadhim, S. A., Chin, J. L., Naganuma, A., Imura, N., and Cherian, M. G. (1993) Modulation of Both Cisplatin Nephrotoxicity and Drug Resistance in Murine Bladder Tumor by Controlling Metallothionein Synthesis. Cancer Res. 53, 1829-1832.

Schaefer, S. D., Post, J. D., Close, L. G., and Wright, C. G. (1985) Ototoxicity of Low- and Moderate-Dose Cisplatin. Cancer 56(8), 1934-9.

Schweitzer, V. G. (1993) Cisplatin-Induced Ototoxicity: The Effect of Pigmentation and Inhibitory Agents. Laryngoscope 103, 1-52.

Stegink, L. D., Bell, E. F., Filer, L. J., Ziegler, E. E. Andersen, D. W. and Seligson, F. H. (1986) Effects of Equimolar Doses of L-Methionine, D-Methionine and L-Methione-dl-Sulfoxide on Plasma and Urinary Amino Acid Levels in Normal Adult Humans. J. Nutr. 116, 1185-1192.

Stewart, D. J., Verma, S., and Maroun, J. A. (1987) Phase I Study of the Combination of Disulfiram With Cisplatin. Am. J. Clin. Oncol. 10(6), 517-519.

Stoter, G., Koopman, A, Vendrik, C. P., Struyvenberg, A., Sleyfer, D. T., Willemse, P. H., Schraffordt, K. H., van Oasterom, A. T., ten Bokkel, Huinink, W. W., & Pinedo, H. M. (1989) Ten-Year Survival and Late Sequelae in Testicular Cancer Patients Treated With Cisplatin, Vinblastine, and Bleomycin. J. Clin. Oncol. 7(8), 1099-104.

Sugihara, K., Nakano, S., and Gemba, M. (1987a) Effect of Cisplatin on In Vitro Production of Lipid Peroxides in Rat Kidney Cortex. Jpn. J. Pharmacol. 44, 71-76.

Tange, R. A., Conijn, EAJG, Van Zeijl LPGM (1982) The Cortitoxic Effect of Cis-Platinum in the Guinea Pig. Arch. Oto-Rhino-Laryngol. (NY) 237, 17-26.

Tognella, S. (1990) Pharmacological Interventions to Reduce Platinum-Induced Toxicity. Cancer Treat. Rev. 17, 139-142.

Treskes, M., and van der Vijgh, W. J. F. (1993) WR2721 As a Modulator of Cisplatin- and Carboplatin-Induced Side Effects in Comparison With Other Chemoprotective Agents: A Molecular Approach. Cancer Chemother. Pharmacol. 33:93-106.

Ugihara, K., Nakano, S., Koda, M., Tanaka, K., Fukuishi, N., and Gemba, M. (1987b) Stimulatory Effect of Cisplatin on Production of Lipid Peroxidation in Renal Tissues. Jpn. J. Pharmacol. 43, 247-252.

Verma, S., Stewart, D. J., Maroun, J. A., and Nair, R. C. (1990) A Randomized Phase II Study of Cisplatin Alone Versus Cisplatin Plus Disulfiram. Am. J. Clin. Oncol. 13:119.

Vermorken, J. B., Kapteijn, T. S., Hart, A. A. M., and Pinedo, H. M. (1983) Ototoxicity of Cis-Diamminedichloro-platinum(II): Influence of Dose, Schedule and Mode of Administration. Eur. J. Cancer Clin. Oncol. 19(1), 53-58.

What is claimed is:

1. A method for preventing or treating ototoxicity in a patient exposed to noise for a time and at an intensity sufficient to result in ototoxicy, the method comprising administering to said patient an effective amount of an otoprotective agent selected from a group consisting of methioninol, hydroxyl methionine, ethionine, a pharmaceutically acceptable salt thereof, and a combination thereof.

2. A method as set forth in claim 1, wherein said otoprotective agent is administered prior to said noise exposure.

3. A method as set forth in claim 1, wherein said otoprotective agent is administered simultaneously with said noise exposure.

4. A method as set forth in claim 1, wherein said otoprotective agent is administered subsequently to said noise exposure.

5. A method as set forth in claim 1, wherein said effective amount of said otoprotective agent is administered to said patient in a time period ranging from about 336 hours before to about 336 hours after said exposure to noise.

6. A method as set forth in claim 5, wherein said effective amount of said otoprotective agent is administered to said patient in a time period ranging from about 48 hours before to about 48 hours after said exposure to noise.

7. A method as set forth in claim 1, wherein said otoprotective agent is administered orally, parenterally, or topically to the round window membrane.

8. A method as set forth in claim 7, wherein the administration of said effective amount of said otoprotective agent results in a blood serum level equivalent to that achieved by parenteral administration in the range of from about 1.0 mg/kg body weight to about 600 mg/kg body weight.

9. A method as set forth in claim 7, wherein the administration of said effective amount of said otoprotective agent results in a blood serum level equivalent to that achieved by parenteral administration in the range of from about 5 mg/kg body weight to about 500 mg/kg body weight.

10. A method as set forth in claim 7, wherein the administration of said effective amount of said otoprotective agent results in a blood serum level equivalent to that achieved by parenteral administration in the range of from about 10 mg/kg body weight to about 400 mg/kg body weight.

11. A method as set forth in claim 1, further comprising administering to said patient a supplemental amount of said otoprotective agent after the administration of said effective amount.

12. A method as set forth in claim 11, wherein said supplemental amount of said otoprotective agent is administered orally, parenterally, or topically to the round window membrane of said patient.

13. A method as set forth in claim 12, wherein the administration of said supplemental amount of said otoprotective agent is sufficient to maintain an effective blood serum level of the otoprotective agent in said patient for a period of from one to fourteen days after the administration of said effective amount.

14. A method as set forth in claim 13, wherein the administration of said supplemental amount of said otoprotective agent is sufficient to maintain a blood serum level of otoprotective agent within said patient of at least about 10% of the blood serum level achieved by administration of the effective amount of said otoprotective agent.

15. A method as set forth in claim 13, wherein the administration of said supplemental amount of said otoprotective agent is sufficient to maintain a blood serum level of otoprotective agent within said patient of from about 20% to about 70% of the blood serum level achieved by administration of the effective amount of said otoprotective agent.

* * * * *